US012642772B2

(12) United States Patent
Velagapudi

(10) Patent No.: US 12,642,772 B2
(45) Date of Patent: Jun. 2, 2026

(54) TRIPTOLIDE FORMULATIONS

(71) Applicant: MINNEAMRITA THERAPEUTICS LLC, Tampa, FL (US)

(72) Inventor: Mohana R. Velagapudi, Tampa, FL (US)

(73) Assignee: MINNEAMRITA THERAPEUTICS LLC, Tampa, FL (US)

( * ) Notice: Subject to any disclaimer, the term of this patent is extended or adjusted under 35 U.S.C. 154(b) by 0 days.

(21) Appl. No.: 19/170,092

(22) Filed: Apr. 4, 2025

(65) Prior Publication Data

US 2025/0255822 A1 Aug. 14, 2025

Related U.S. Application Data

(63) Continuation of application No. PCT/US2025/011417, filed on Jan. 13, 2025.

(60) Provisional application No. 63/619,900, filed on Jan. 11, 2024.

(51) Int. Cl.
*A61K 9/20* (2006.01)
*A61K 31/365* (2006.01)

(52) U.S. Cl.
CPC .......... *A61K 9/2054* (2013.01); *A61K 9/2009* (2013.01); *A61K 9/2018* (2013.01); *A61K 31/365* (2013.01)

(58) Field of Classification Search
None
See application file for complete search history.

(56) References Cited

U.S. PATENT DOCUMENTS

| | | | |
|---|---|---|---|
| 6,548,537 B1 | 4/2003 | Dai et al. | |
| 8,507,552 B2 | 8/2013 | Georg et al. | |
| 9,150,600 B2 | 10/2015 | Georg et al. | |
| 9,545,361 B1 | 1/2017 | Brough | |
| 9,623,035 B2 | 4/2017 | Georg et al. | |
| 10,265,301 B2 | 4/2019 | Miller et al. | |
| 10,328,050 B2 | 6/2019 | Astsaturov et al. | |
| 10,695,319 B2 | 6/2020 | Liu et al. | |
| 10,709,725 B2 | 7/2020 | Li | |
| 11,007,194 B2 | 5/2021 | Stuart et al. | |
| 11,306,070 B2 | 4/2022 | Gray et al. | |
| 11,878,005 B2 | 1/2024 | Miller et al. | |
| 2007/0092585 A1 | 4/2007 | Skinner | |
| 2009/0053315 A1 | 2/2009 | Brough et al. | |
| 2011/0045102 A1 | 2/2011 | Skinner | |
| 2016/0354339 A1 | 12/2016 | Astsaturov et al. | |
| 2017/0020824 A1 | 1/2017 | Desai et al. | |
| 2017/0258917 A1* | 9/2017 | Subbiah | A61K 47/44 |
| 2019/0133963 A1 | 5/2019 | Kharbanda et al. | |
| 2019/0142756 A1 | 5/2019 | Miller et al. | |
| 2019/0167643 A1 | 6/2019 | Miller et al. | |
| 2019/0321305 A1 | 10/2019 | Kharbanda et al. | |
| 2020/0002412 A1 | 1/2020 | Hendifar | |
| 2020/0009060 A1 | 1/2020 | Miller et al. | |
| 2020/0071415 A1 | 3/2020 | Cronier et al. | |
| 2020/0085784 A1 | 3/2020 | Saluja et al. | |
| 2020/0297693 A1 | 9/2020 | Liu et al. | |
| 2021/0000778 A1 | 1/2021 | Luther et al. | |
| 2021/0128536 A1 | 5/2021 | Williams, III et al. | |
| 2021/0196730 A1 | 7/2021 | Qian et al. | |
| 2021/0205286 A1 | 7/2021 | Deretic et al. | |
| 2021/0267922 A1 | 9/2021 | Luther et al. | |
| 2021/0315911 A1 | 10/2021 | Shen et al. | |
| 2021/0380988 A1 | 12/2021 | Mercurio et al. | |
| 2023/0038138 A1 | 2/2023 | Hattersley et al. | |
| 2023/0301924 A1 | 9/2023 | Zhu et al. | |
| 2024/0091201 A1 | 3/2024 | Miller et al. | |

FOREIGN PATENT DOCUMENTS

| | | | |
|---|---|---|---|
| CN | 105434446 A | 3/2016 | |
| CN | 111032043 A | 4/2020 | |
| CN | 112839675 A | 5/2021 | |
| WO | WO-03063831 A2 * | 8/2003 | A61P 43/00 |
| WO | 2012009388 A1 | 1/2012 | |
| WO | 2014167581 A2 | 10/2014 | |
| WO | 2016073421 A1 | 5/2016 | |
| WO | 2016205658 A1 | 12/2016 | |
| WO | 2019094688 A1 | 5/2019 | |
| WO | 2020023439 A1 | 1/2020 | |
| WO | 2021108022 A1 | 6/2021 | |

OTHER PUBLICATIONS

Zhu et al. (Drug Delivery, vol. 29, No. 1, 1398-1408) (Year: 2022).*
Bhujbal et al. (Journal of Pharmaceutical Sciences 110, 2423-2431). (Year: 2021).*
Borazanci et al., "First-in-Human Phase I Study of Minnelide in Patients With Advanced Gastrointestinal Cancers: Safety, Pharmacokinetics, Pharmacodynamics, and Antitumor Activity," The Oncologist, 29, 132-14, Jan. 2024.
Clinical Trial NCT03129139, A Phase 1, Multi-Center, Open-Label, Dose-Escalation, Safety, Pharmacokinetic, and Pharmacodynamic Study with Protein-Bound Paclitaxel in Patients with Advanced Solid Tumors (Minnelide 101), Retrieved from https://beta.clinicaltrials.gov/study/NCT03129139; 12pgs, Apr. 6, 2022.
International Search Report & Written Opinion of the ISA/US dated Mar. 19, 2025 in International Application No. PCT/US2025/011417; 10pgs.
Lee et al., "Phase I study of Minnelide and paclitaxel combination chemotherapy in refractory gastric cancer (GC)", Journal of Clinical Oncology 41, No. 4, p. 414, Feb. 1, 2023.

(Continued)

*Primary Examiner* — Tigabu Kassa
(74) *Attorney, Agent, or Firm* — Haukaas Fortius PLLC; Michael H. Haukaas; Raymond F. Horvath

(57) ABSTRACT

A pharmaceutical composition containing triptolide or a derivative thereof, as well as methods of using the composition and methods of manufacturing the composition. The composition can be prepared using thermokinetic compounding and can provide improved properties, such as improved bioavailability. The composition can improve the therapeutic treatment of cancers such as pancreatic cancer, breast cancer, bladder cancer, kidney cancer, ovarian cancer, glioblastoma, or melanoma.

10 Claims, 6 Drawing Sheets

(56) References Cited

OTHER PUBLICATIONS

Lim et al., "The safety and efficacy outcomes of Minnelide given alone or in combination with paclitaxel in advanced gastric cancer: A phase I trial."
Modi et al., "Minnelide synergizes with conventional chemotherapy by targeting both cancer and associated stroma components in pancreatic cancer," Cancer Letters, vol. 537, 215591, Apr. 2022.
Modi et al., "Triptolide in Combination with Low Dose Gemcitabine and Nab-Paclitaxel: A Novel Effective Combination Chemotherapy Regiment for Pancreatic Cancer," Scientific Forum: 2016 Clinical Congress., vol. 223, No. 4S2, e49, Oct. 2016.
Park et al., "A phase 1b, open-label, safety, pharmacokinetic, and pharmacodynamic study of an anti super-enhancer triptolide analogue with nab-paclitaxel plus gemcitabine in patients with metastatic adenocarcinoma of the pancreas," Journal of Clinical Oncology., vol. 41, No. 4 suppl., Meeting Abstract, pTPS769, Feb. 2023.
Wang et al., "The enhanced antitumor effect of combined triptolide and paclitaxel on pancreatic cancer call lines," J. Clin. Oncol., 32, 335-335, Jan. 2014.
Zeng et al., "Pharmacological activity and clinical progress of Triptolide and its derivatives LLDT-8, PG490-88Na, and Minnelide: a narrative review," Eur. Rev. Med. Pharmacol. Sci., 27(21): 10181-10203, Nov. 2023.
Zhang et al., "Phase I/II study of albumin-bound nab-paclitaxel plus gemcitabine administered to Chinese patients with advanced pancreatic cancer," Cancer Chemother Pharmacol., 71:1065-1072, Mar. 2013.

* cited by examiner

Mean Triptolide Concentration vs Time Profile: Linear Scale (N = 4)

Mean Triptolide Concentration vs Time Profile: Semilogarithmic Scale (N = 4)

TRIPTOLIDE FORMULATIONS

RELATED APPLICATIONS

This application is a continuation under 35 U.S.C. § 111(a) of International Application No. PCT/US2025/011417, filed Jan. 13, 2025, which claims priority under 35 U.S.C. § 119(e) to U.S. Provisional Patent Application No. 63/619,900, filed Jan. 11, 2024, which applications are incorporated herein by reference.

BACKGROUND OF THE INVENTION

Triptolide is a naturally occurring diterpene obtained from the plant *Tripterygium wilfordii*. It has been shown to inhibit tumor cell proliferation and induce apoptosis in vitro and in animal models of cancer, including human mammary tumors, cholangio-carcinoma cells, xenografts of several different tumor types, including melanoma, breast cancer, bladder cancer, gastric carcinoma, pancreatic tumors, and neuroblastoma. The antitumor effect of triptolide is the result of inhibition of heat shock protein (HSP)70 expression in tumor cells and induction of apoptosis. While the mechanism of action of triptolide inhibition of HSP70 expression has not been fully elucidated, it has been shown to induce caspase activation.

One disadvantage associated with using triptolide as a therapeutic is its poor solubility in water (approximately 0.017 mg/mL). Another problem associated with natural triptolide is poor bioavailability when administered orally or intravenously. Triptolide, triptolide derivatives, and certain prodrugs having improved solubility and reduced toxicity are known. For example, U.S. Pat. No. 6,548,537 (Dai et al.) and U.S. Pat. No. 8,507,552 (Georg et al.) describe triptolide prodrugs having increased solubility and reduced toxicity.

Despite the availability of these improvements, there continues to be a medical need for novel therapeutic formulations and treatment regimens that are even more stable and bioavailable, and thus more effective than the therapeutic formulations currently available.

SUMMARY

The invention provides a pharmaceutical composition comprising an amorphous solid dispersion of a compound formula I:

(I)

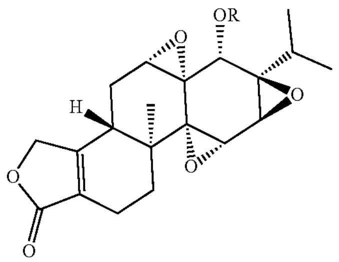

;

wherein R is H, $—CH_2O(PO_3H_2)$, or a salt of $—CH_2O(PO_3H_2)$ (e.g., a salt of $—CH_2O(PO_3X_2)$ wherein each X is independently H or a pharmaceutically acceptable cation such as sodium or potassium); and one or more pharmaceutically acceptable excipients; wherein the composition has a single glass transition temperature. In one embodiment, the compound is triptolide.

The invention also provides a pharmaceutical composition comprising an amorphous solid dispersion of triptolide and one or more pharmaceutically acceptable excipients. The composition can have a single glass transition temperature and the composition can remain amorphous per x-ray diffraction analysis following storage in an open container at about 40° C. with a relative humidity of about 75%, at five weeks.

In one embodiment, the pharmaceutical composition comprises about 0.1 mg to about 1 mg of triptolide. In other embodiments, the pharmaceutical composition comprises about 0.1 mg of triptolide, about 0.15 mg of triptolide, about 0.2 mg of triptolide, about 0.25 mg of triptolide, about 0.4 mg of triptolide, about 0.5 mg of triptolide, or about 0.6 mg of triptolide.

In some embodiments, the one or more pharmaceutically acceptable excipients comprise a processing agent, one or more polymers, and a lubricant. The processing agent can be a processing agent selected from the group consisting of sodium carboxymethyl-cellulose, poly(vinylpyrrolidone), hydroxypropylcellulose, poly(vinyl alcohol), hydroxypropyl methylcellulose, hydroxyethylcellulose, and polyvinyl caprolactam-polyvinyl acetate-polyethylene glycol graft copolymer. The one or more polymers can comprise one or more water-soluble polymers selected from the group consisting of hydroxypropyl-methylcellulose acetate succinate, poly(vinyl acetate)-co-poly(vinylpyrrolidone) copolymer, poly(vinylpyrrolidone), cellulose acetate phthalate, poly(vinyl acetate) phthalate, hydroxypropyl-methylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropyl methylcellulose, poly(vinyl alcohol), and polyvinyl caprolactam-polyvinyl acetate-polyethylene glycol graft copolymer. The lubricant can be a non-polymeric lubricant, wherein the non-polymeric lubricant is rendered amorphous in an internal phase of the amorphous solid dispersion of the pharmaceutical composition. In some embodiments, the lubricant comprises magnesium, stearic acid, a stearate, or a fumarate. In certain specific embodiments, is magnesium stearate or sodium stearyl fumarate.

In some embodiments, the composition comprises less than 1% degradation products of triptolide and in various embodiments, the pharmaceutical composition does not contain a processing agent, and/or does not contain a plasticizer. In further embodiments, the one or more pharmaceutically acceptable excipients comprises pharmaceutical polymer of high melt viscosity or a thermally labile pharmaceutical polymer.

The pharmaceutical composition can be formulated as an oral dosage form, optionally in the form of a tablet, a capsule, or a sachet. The oral dosage form can also be an extended-release form, an immediate release form, a disintegrating tablet or an eroding tablet.

The invention further provides a pharmaceutical composition comprising an amorphous solid dispersion of triptolide and one or more pharmaceutically acceptable excipients, wherein the one or more pharmaceutically acceptable excipients comprise a processing agent, one or more polymers, and a lubricant; wherein the composition consists essentially of:

about 0.1 mg to about 1 mg of triptolide;

sodium carboxymethylcellulose, hydroxypropyl-methylcellulose acetate succinate, cellulose, mannitol, and a non-polymeric lubricant, wherein the non-polymeric lubricant is rendered amorphous in an internal phase of the amorphous solid dispersion of the pharmaceutical composition; and wherein the composition has a single glass transition temperature and the composition remains amorphous per x-ray diffraction analysis following storage in an open container at about 40° C. with a relative humidity of about 75% at five weeks.

The pharmaceutical composition can comprise about 0.5% w/w to about 1.5% w/w non-polymeric lubricant. In some embodiments, the lubricant is magnesium stearate or sodium stearyl fumarate.

The invention additionally provides a method of increasing the bioavailability of triptolide comprising formulating triptolide into the amorphous solid dispersion pharmaceutical composition described herein and administering the pharmaceutical composition to the cancer patient, thereby providing triptolide to the cancer patient in a manner that provides greater bioavailability of triptolide than when triptolide is administered in a composition that is not an amorphous solid dispersion having a single glass transition temperature. The invention yet further provides a method of treating cancer comprising administering to a cancer subject in need thereof an effective anticancer amount of the pharmaceutical composition described herein, thereby treating the cancer, wherein the triptolide is optionally administered in a dosing regimen as described, and is optionally administered in combination with a second active agent according to a dosing regimen described herein. In some embodiments, the cancer comprises gastric cancer, pancreatic cancer, breast cancer, bladder cancer, kidney cancer, lung cancer, ovarian cancer, glioblastoma, or melanoma.

The invention thus provides a method for treating cancer (e.g., pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors) in a mammal (e.g., a human), comprising administering the pharmaceutical composition comprising a compound of formula I, or a pharmaceutically acceptable salt thereof, to the mammal (e.g., a human).

The invention also provides the use of the composition comprising a compound of formula I, or a pharmaceutically acceptable salt thereof, for the manufacture of a medicament for the treatment of cancer (e.g., pancreatic cancer, bile duct carcinoma, neuroblastoma, colon cancer, breast cancer, myeloma, gastric cancer, liver cancer, glioblastoma, ovarian cancer, colorectal cancer, non-Hodgkin lymphoma, lung cancer, prostate cancer, small-cell lung cancer, large cell lung cancer, kidney cancer, esophageal cancer, stomach cancer, cervical cancer or lymphoma tumors.) in a mammal (e.g., a human).

The invention also provides a method for inhibiting cancer cell growth in an HSP70-expressing cancer (e.g., pancreatic cancer, neuroblastoma, breast cancer, colon cancer, gastric cancer, liver cancer or glioblastoma) in a mammal (e.g., a human) comprising administering an inhibitory effective amount of the composition comprising a compound of formula I, or a pharmaceutically acceptable salt thereof, to the mammal (e.g., a human).

The invention also provides the composition comprising a compound of formula I, or a pharmaceutically acceptable salt thereof, for use in the prophylactic or therapeutic inhibition of cancer cell growth in an HSP70-expressing cancer (e.g., pancreatic cancer, neuroblastoma, breast cancer, colon cancer, gastric cancer, liver cancer or glioblastoma).

The invention also provides the use of the composition comprising a compound of formula I, or a pharmaceutically acceptable salt thereof, for the manufacture of a medicament for the inhibition of cancer cell growth in an HSP70-expressing cancer (e.g. pancreatic cancer, neuroblastoma, breast cancer, colon cancer, gastric cancer, liver cancer or glioblastoma) in a mammal (e.g. a human).

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

In each of FIGS. 2-3 and 5-6, dogs are identified by the 100x number to clearly indicate the same dog received both treatments.

Figure 2A:
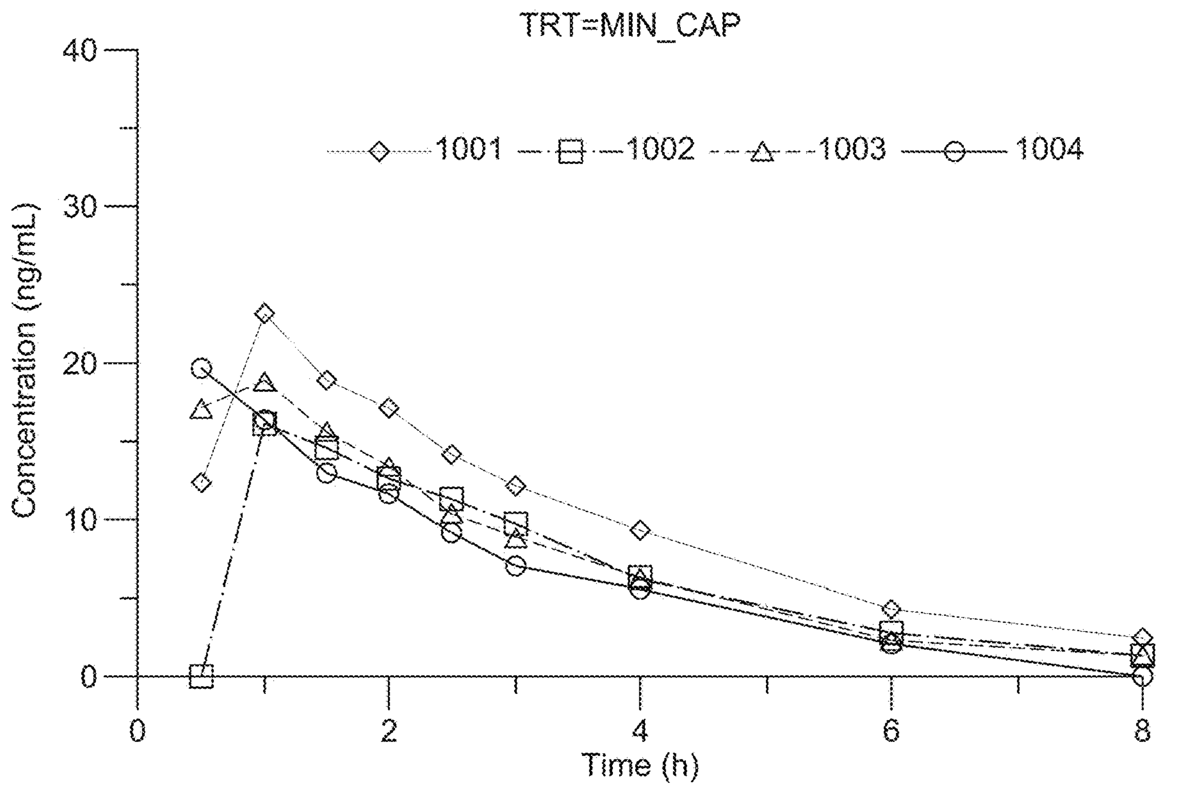
Figure 2B:
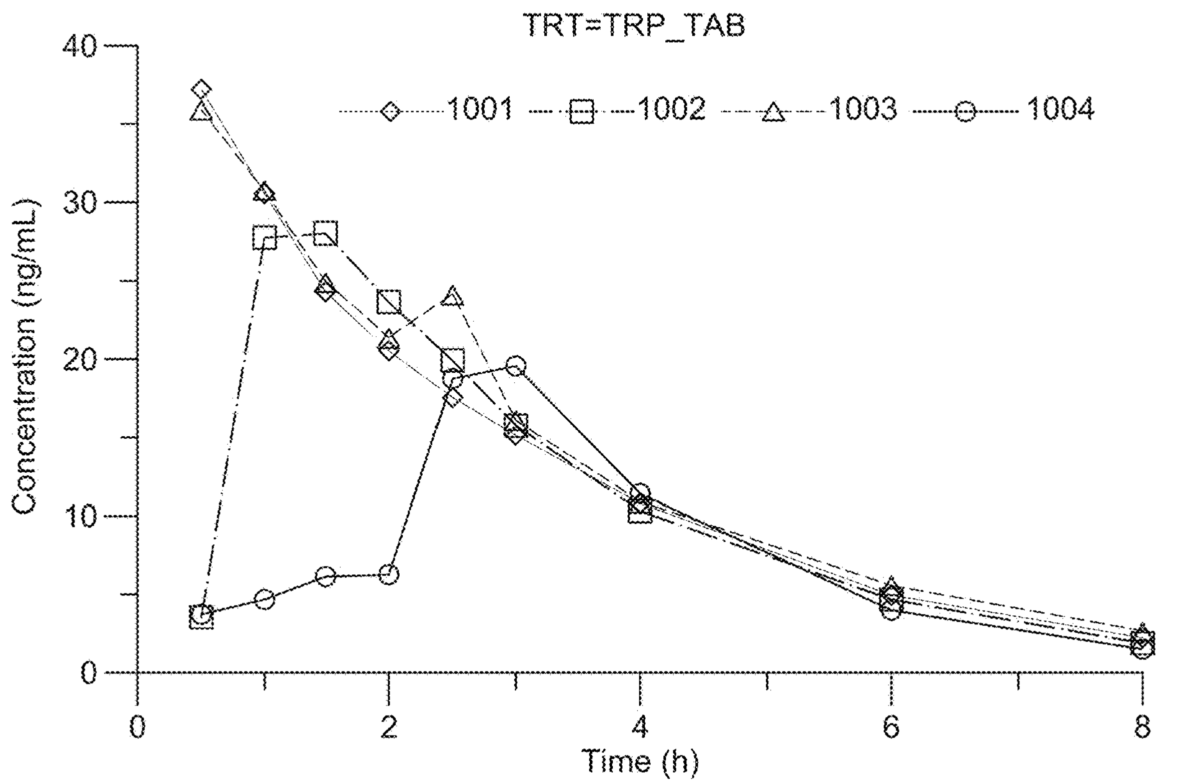

FIG. 2A-B. Triptolide Concentration vs Time Profiles for Individual Dogs (Linear Scale). A: Treatment (TRT)=minnelide capsule (MIN_CAP); B: treatment=triptolide tablet (TRP_TAB).

Figure 3A:
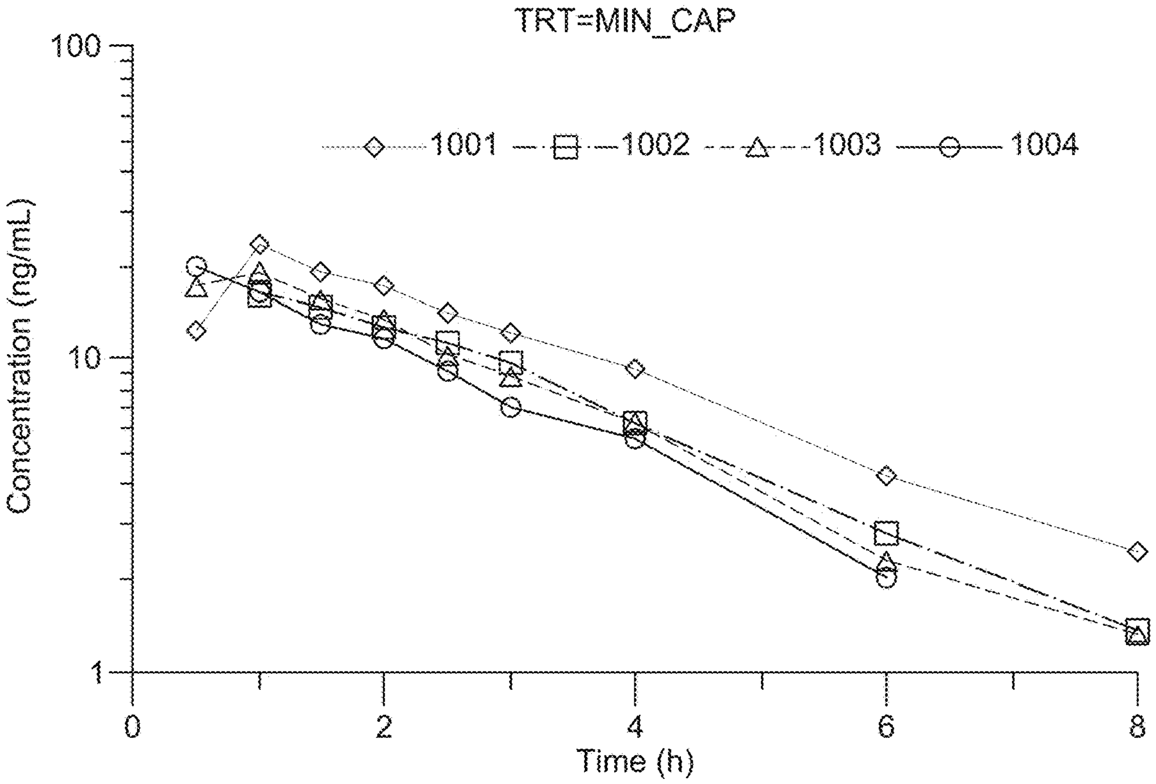
Figure 3B:
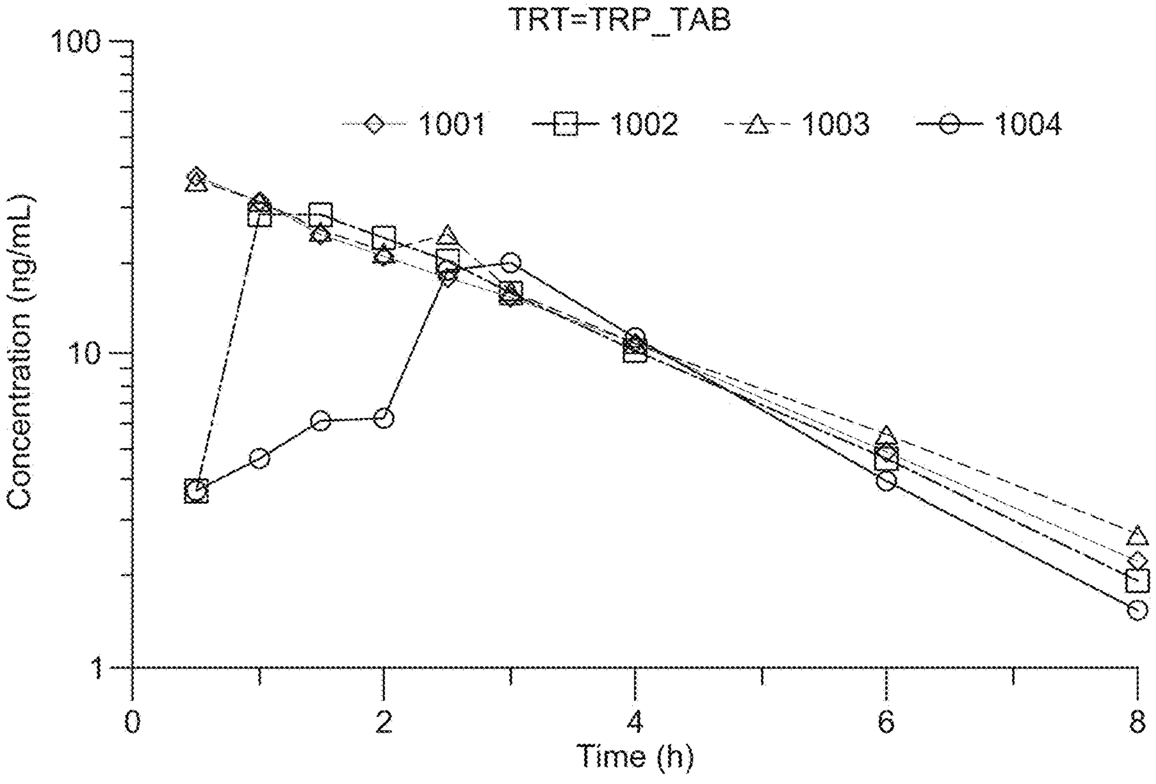

FIG. 3A-B. Triptolide Concentration vs Time Profiles for Individual Dogs (Semilogarithmic Scale). A: Treatment (TRT)=minnelide capsule (MIN_CAP); B: treatment=triptolide tablet (TRP TAB).

Figure 4A:
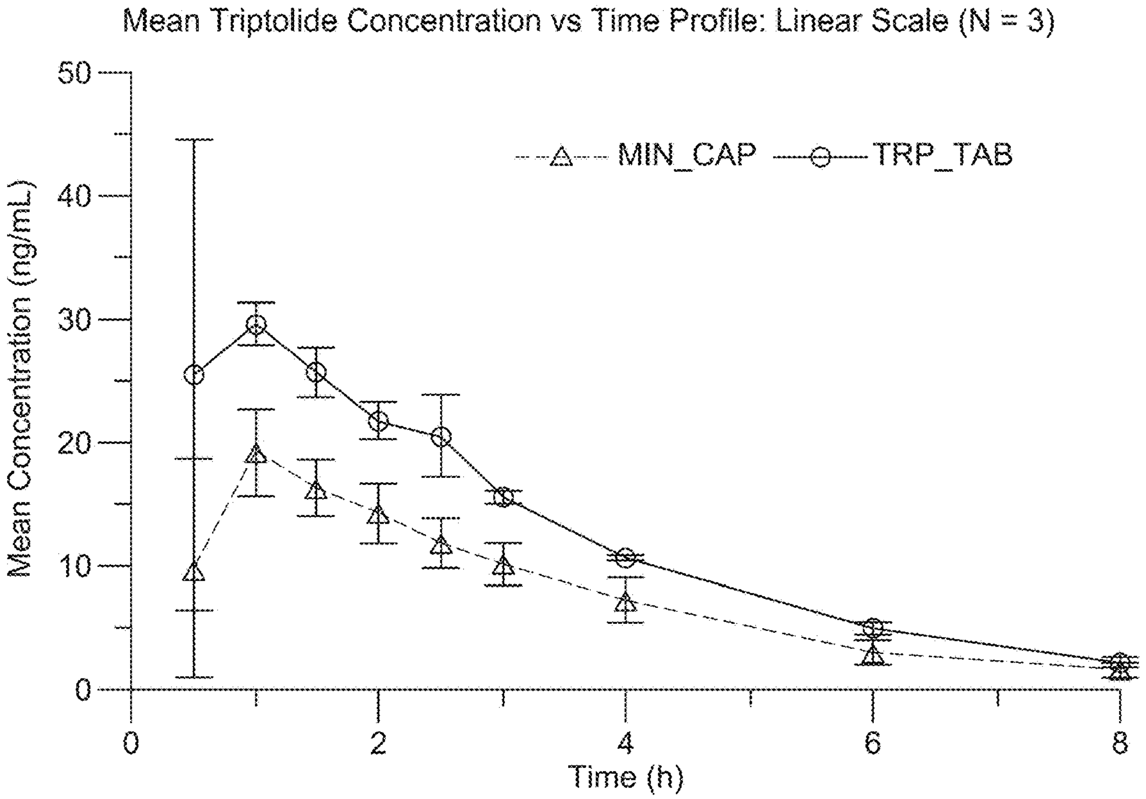
Figure 4B:
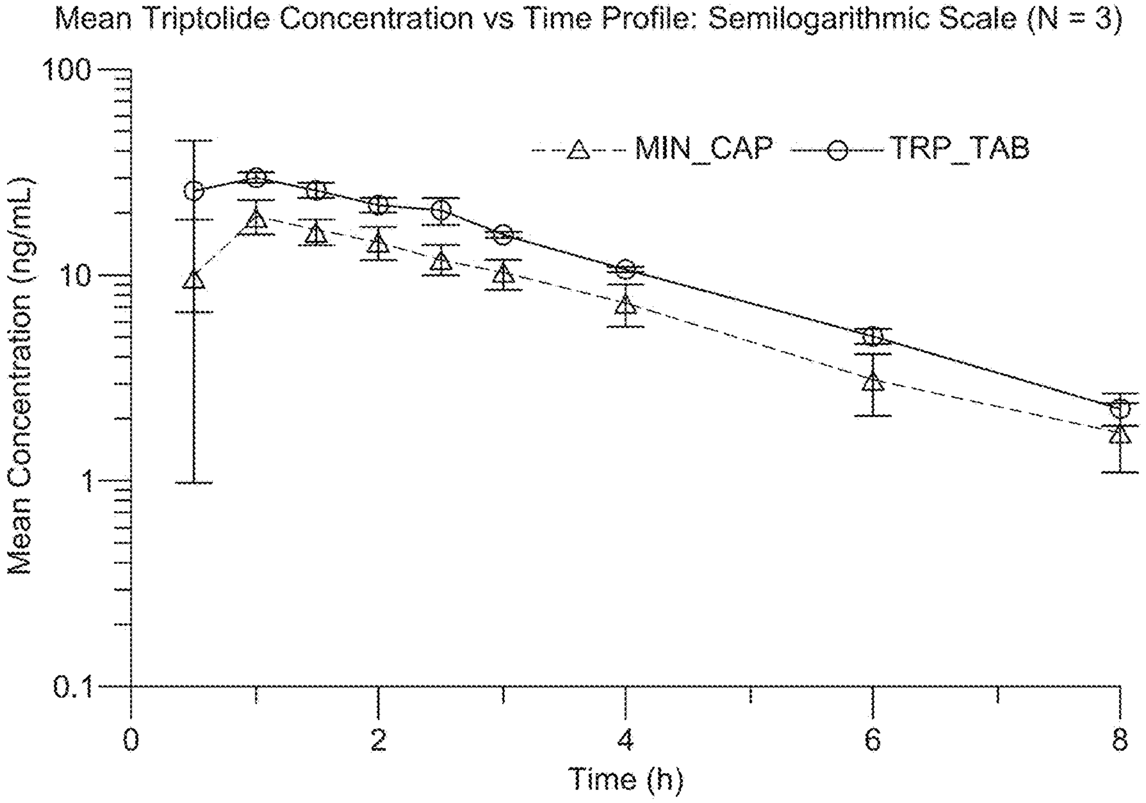

FIG. 4A-B. PK Analysis Results: Analysis Excluding Dog 1004. Mean Triptolide Concentration vs Time Profiles (N=3). A: Linear Scale; B: Semilogarithmic Scale. Dog 1004 was excluded (both treatments).

Figure 5A:
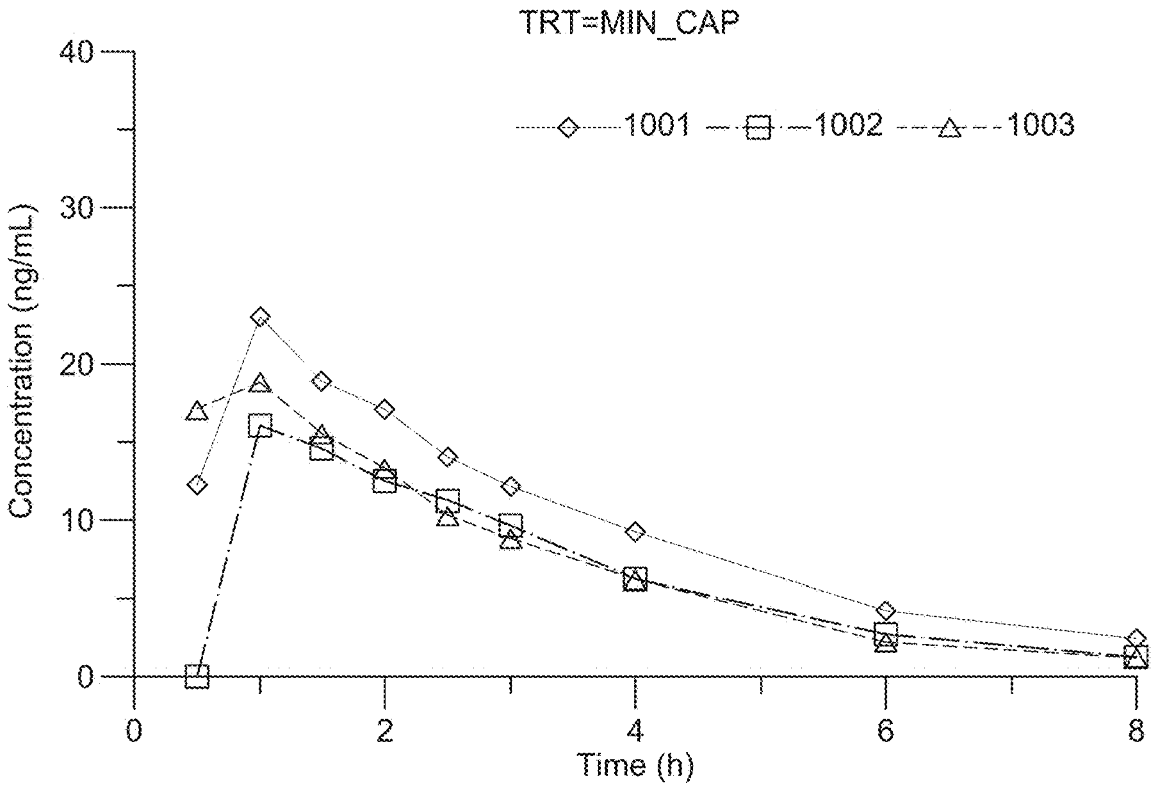
Figure 5B:
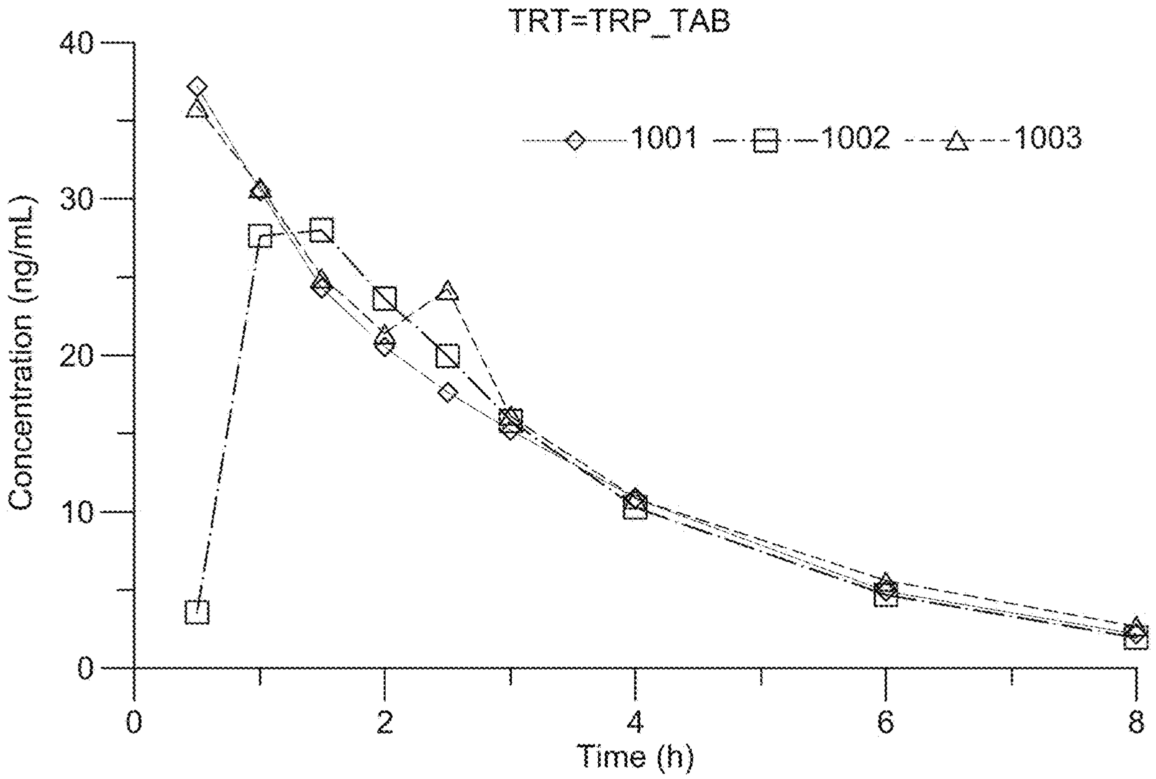

FIG. 5A-B. PK Analysis Results: Analysis Excluding Dog 1004. Triptolide Concentration vs Time Profiles for Individual Dogs (Linear Scale). A: Treatment (TRT)=minnelide capsule (MIN_CAP); B: treatment=triptolide tablet (TRP_TAB).

Figure 6A:
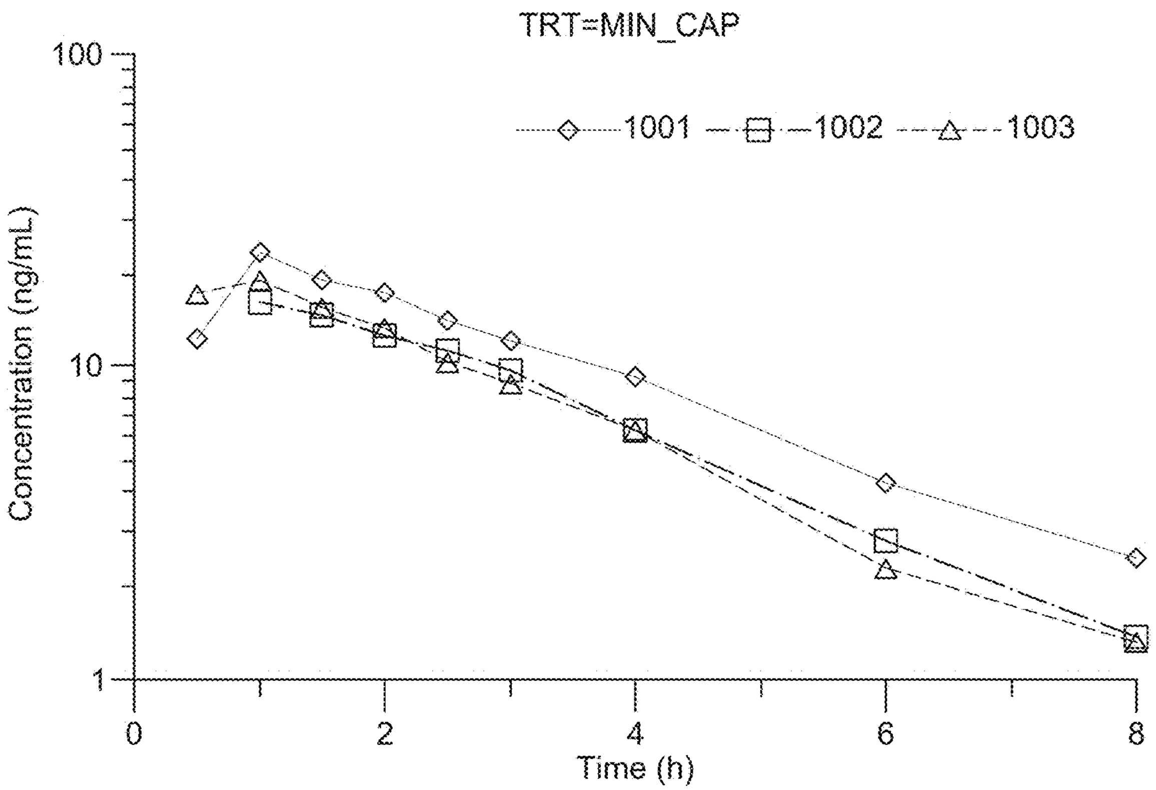
Figure 6B:
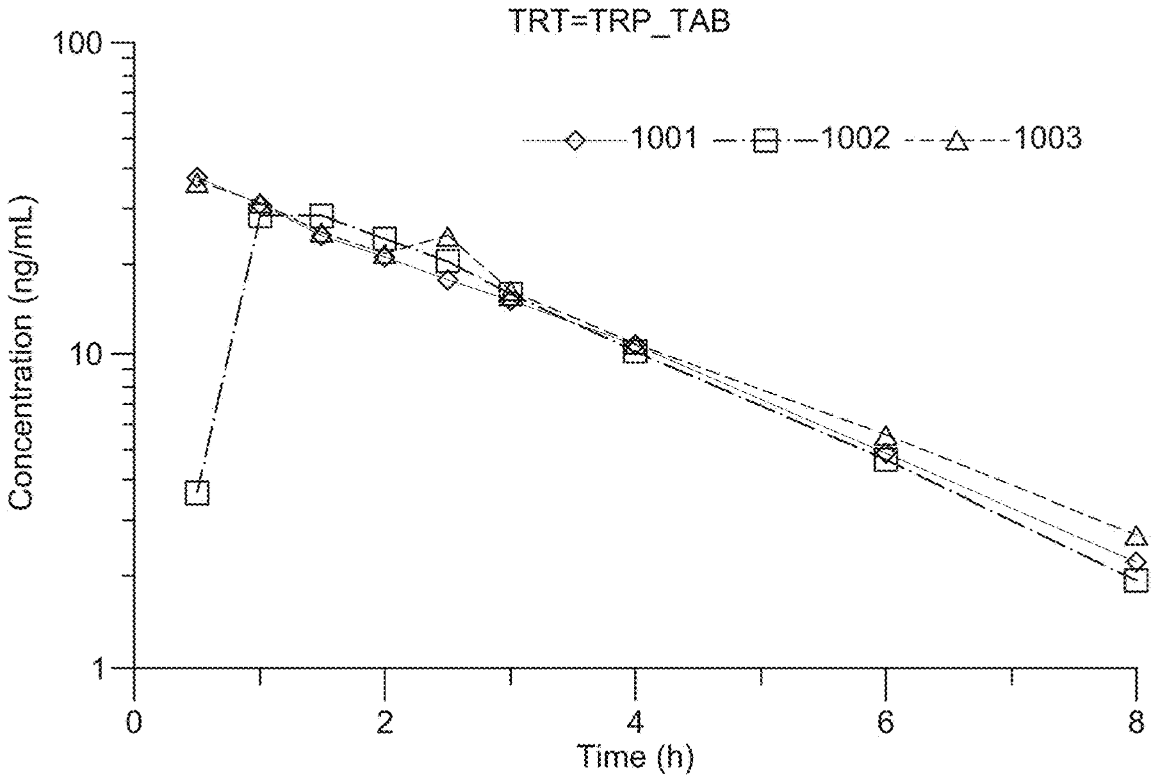

FIG. 6A-B. PK Analysis Results: Analysis Excluding Dog 1004. Triptolide Concentration vs Time Profiles for Individual Dogs (Semilogarithmic Scale). A: Treatment (TRT)=minnelide capsule (MIN_CAP); B: treatment=triptolide tablet (TRP_TAB).

DETAILED DESCRIPTION

Described herein is a formulation that allows for triptolide and triptolide prodrug compounds to achieve improved aqueous solubility, effective bioavailability for oral dosage forms, faster in vivo release of triptolide, and relatively reduced or lower toxicity in combination with significant inhibition of cancer cell growth. Accordingly, the triptolide formulation described herein provides improved solubility, bioavailability, and stability, compared to known triptolide formulations. The formulation can be in the form of an oral dosage unit, such as a tablet, capsule, or pill. The amount of triptolide in each tablet can be adjusted according to the desired strength but is typically about 0.5 mg per tablet, or as otherwise recited herein.

Accordingly, described herein are improved triptolide compositions and methods for their manufacture. The methods permit thermal processing to produce an amorphous solid dispersion of triptolide with high amorphous drug loading. The high melting point of triptolide precludes the use of other thermal processing technologies, namely melt extrusion, for the production the amorphous dispersion compositions described herein because the processing temperatures required to achieve high-drug load triptolide amorphous dispersions would exceed the degradation temperatures of the polymers. Moreover, the prolonged processing times of a typical melt extrusion process at the temperatures required to form a high drug load triptolide amorphous dispersion are expected to result in the generation of high drug-related impurities content (>1%). Moreover, the non-solvent nature of the methods eliminates issues associated with solvent-based processes, namely, cost, safety, and environmental waste. Furthermore, the methods are vastly more efficient than the leading solvent-based processes; namely, spray drying; owing to the limited solubility of triptolide in common volatile organic solvents, which leads to copious amounts of solvent evaporation to obtain relatively small amounts of solids. The methods of the current disclosure permit unique amorphous dispersion compositions of triptolide with an array of pharmaceutical carriers including ionic, non-ionic, cross-linked, highly viscous, and thermally labile pharma polymers with additional advantages in drug manufacture and delivery.

Using the processing methods described herein, enhanced dissolution kinetics and mitigation of pH-dependent solubility of triptolide by the amorphous solid dispersion formulations are achieved, resulting in improved pharmacokinetic (PK) profiles relative to compositions containing crystalline triptolide. For example, increased total oral absorption (AUC) of triptolide, increased peak plasma concentrations ($C_{max}$) of triptolide, reduced PK variability, mitigated food effect, complete and consistent absorption in human subjects relative to compositions containing crystalline triptolide, and enhanced triptolide efficacy in patients that poorly absorb crystalline forms of the compound can all be achieved.

Because the triptolide dissolution and solubility enhancement achieved with the compositions described herein are superior to the currently available compositions, these new formulations will enable therapeutic concentrations to be achieved at substantially lower doses in patients that have been previously identified to be inadequate responders to triptolide when administered orally in a substantially crystalline form or other known formulations. This will improve the efficacy of triptolide in these patients by achieving therapeutic blood levels at reasonable doses and enabling more rapid and consistent dose titration, as well as improve the safety profile of triptolide in these patients as these formulations will substantially reduce the administered dose and consequently the frequency and severity of adverse events.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of: ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

The recitation of a), b), c), . . . or i), ii), iii), or the like in a list of components or steps do not confer any particular order unless explicitly stated.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, the patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified.

For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps.

As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

As used herein, the term "thermokinetic compounding" or "TKC" refers to a method of thermokinetic mixing until melt blended. TKC may also be described as a thermokinetic mixing process or thermokinetic processing in which processing ends at a point sometime prior to agglomeration.

As used herein, the phrase "a homogenous, heterogenous, or heterogeneously homogenous composite or an amorphous composite" refers to the various compositions that can be made using the TKC method.

As used herein, the term "heterogeneously homogenous composite" refers to a material composition having at least two different materials that are evenly and uniformly distributed throughout the volume.

As used herein, the phrase "reference standard active pharmaceutical ingredient" means the most thermodynamically stable form of the active pharmaceutical ingredient that is currently available.

As used herein, the term "substantial degradation," in conjunction with triptolide or "additional API(s)" refers to degradation leading to the generation of impurities at levels beyond the threshold that has been qualified by toxicology studies, or beyond the allowable threshold for unknown impurities. See, for example Guidance for Industry, Q3B (R2) Impurities in New Drug Products (International Committee for Harmonization, published by the U.S. Department of Health and Human Services, Food and Drug Administration, Center for Drug Evaluation and Research (CDER), Center for Biologics Evaluation and Research), July 2006. As used herein, the term "substantial degradation," in conjunction with the term "excipient" refers to decomposition of the excipient to the extent that the excipient would no longer meet the specifications set forth in an official monograph of an accepted pharmacopeia, e.g., the United States Pharmacopeia.

As used herein, the term "high melt viscosity" refers to melt viscosities greater than 10,000 Pa*s.

As used herein, the term "thermally labile API" refers to an API (active pharmaceutical ingredient) that degrades at its crystalline melting point, or one that degrades at temperatures below the crystalline melting point when in a non-crystalline (amorphous) form. As used herein, the term "thermolabile polymer" refers to a polymer that degrades at or below about 200° C.

Whether the composition of the present disclosure is a homogenous, heterogenous, or heterogeneously homogenous composition, an amorphous composition or combinations thereof, the thermokinetic compounding (TKC) processing conditions can produce a composition with a glass transition temperature that is higher than the glass transition temperature of an identical combination of the drug and pharmaceutically acceptable excipients, adjuvants, additional APIs, or any combination thereof, thermally processed or processed using the microprecipitated bulk powder (MBP) method, for example, either with or without the use of a plasticizer. The TKC processing conditions can also produce a composition with a single glass transition temperature, wherein an identical combination of the identical API and pharmaceutically acceptable excipients, adjuvants, additional APIs, or any combination thereof, processed thermally has two or more glass transition temperatures.

In other embodiments, the pharmaceutical compositions of the present disclosure have a single glass transition temperature that is at least about 50%, 60%, 70%, 80%, or 90% higher than the lowest glass transition temperature of the identical combination processed thermally. Alternatively, the compositions made using thermokinetic processing may generate compositions with a minimum of at least about 90%, 91%, 92%, 93%, 94%, 95%, 96%, 97%, 98%, 99%, or 99.9% therapeutic potency with respect to each drug.

As used herein, the term "thermokinetic chamber" refers to an enclosed vessel or chamber in which the TKC method is used to make the novel compositions of the present disclosure.

As used herein, "thermally processed" or "processed thermally" means that components are processed by hot melt extrusion, melt granulation, compression molding, tablet compression, capsule filling, film-coating, or injection molding.

As used herein, "extrusion" is the well-known method of applying pressure to a damp or melted composition until it flows through an orifice or a defined opening. The extrudable length varies with the physical characteristics of the material to be extruded, the method of extrusion, and the process of manipulation of the particles after extrusion. Various types of extrusion devices can be employed, such as screw, sieve and basket, roll, and ram extruders. Furthermore, the extrusion can be carried out through melt extrusion. Components of the present disclosure can be melted and extruded with a continuous, solvent free extrusion process, with or without inclusion of additives. Such processes are well-known to skilled practitioners in the art.

As used herein, "spray congealing" is a method that is generally used in changing the structure of materials, to obtain free flowing powders from liquids and to provide pellets. Spray congealing is a process in which a substance of interest is allowed to melt, disperse, or dissolve in a hot melt of other additives, and is then sprayed into an air chamber wherein the temperature is below the melting point of the formulation components, to provide congealed pellets. Such a process is well-known to skilled practitioners in the art.

As used herein, "solvent dehydration" or "spray drying technique" is commonly employed to produce a dry powder from a liquid or slurry by rapidly drying with a hot gas. This is one preferred method of drying many thermally sensitive materials such as foods and pharmaceuticals. Water or organic solvent-based formulations can be spray dried by using inert process gas, such as nitrogen, argon and the like. Such a process is well-known to skilled practitioners in the art.

As used herein, "bioavailability" is a term meaning the degree to which a drug becomes available to the target tissue after being administered to the body. Poor bioavailability is a significant problem encountered in the development of pharmaceutical compositions, particularly those containing a drug that is not highly soluble.

As used herein, the phrase "pharmaceutically acceptable" refers to molecular entities, compositions, materials, excipients, carriers, and the like that do not produce an allergic or similar untoward reaction when administered to humans in general.

As used herein, "poorly soluble" refers to drug having a solubility such that the dose to be administered cannot be fully dissolved in 250 mL of aqueous media ranging in pH from 1 to 7.5, a drug with a slow dissolution rate, and a drug with a low equilibrium solubility, for example resulting in decreased bioavailability of the pharmacological effect of the therapeutic drug being delivered.

As used herein, "derivative" refers to chemically modified inhibitors or stimulators that still retain the desired effect or property of the original drug. Such derivatives may be derived by the addition, removal, or substitution of one or more chemical moieties on the parent molecule. Such moieties may include, but are not limited to, an element such as a hydrogen or a halide, or a molecular group such as a methyl group. Such a derivative may be prepared by any method known to those of skill in the art. The properties of such derivatives may be assayed for their desired properties by any means known to those of skill in the art. As used herein, "analogs" include structural equivalents or mimetics.

The solution agent used in the solution can be aqueous such as water, one or more organic solvents, or a combination thereof. When used, the organic solvents can be water miscible or non-water miscible. Suitable organic solvents include but are not limited to ethanol, methanol, tetrahydrofuran, acetonitrile, acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, and combinations thereof.

By "immediate release" is meant a release of an API to an environment over a period of seconds to no more than about 30 minutes once release has begun and release begins within no more than about 2 minutes after administration. An immediate release does not exhibit a significant delay in the release of drug.

By "rapid release" is meant a release of an API to an environment over a period of 1-59 minutes or 0.1 minute to three hours once release has begun and release can begin within a few minutes after administration or after expiration of a delay period (lag time) after administration.

As used herein, the term "extended release" profile assumes the definition as widely recognized in the art of pharmaceutical sciences. An extended-release dosage form will release an API at a substantially constant rate over an extended period of time or a substantially constant amount of API will be released incrementally over an extended period of time. An extended-release tablet generally effects at least a two-fold reduction in dosing frequency as compared to the API presented in a conventional dosage form (e.g., a solution or rapid releasing conventional solid dosage forms).

By "controlled release" is meant a release of an API to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered.

The term "controlled release", as regards to drug release, includes the terms "extended release," "prolonged release," "sustained release," or "slow release," as these terms are used in the pharmaceutical sciences. A controlled release can begin within a few minutes after administration or after expiration of a delay period (lag time) after administration.

A "slow release dosage form" is one that provides a slow rate of release of API so that API is released slowly and approximately continuously over a period of 3 hours, 6 hours, 12 hours, 18 hours, a day, 2 or more days, a week, or 2 or more weeks.

The term "mixed release" as used herein refers to a pharmaceutical agent that includes two or more release profiles for one or more active pharmaceutical ingredients. For example, the mixed release may include an immediate release and an extended-release portion, each of which may be the same API or each may be a different API.

A "timed release dosage form" is one that begins to release an API after a predetermined period of time as measured from the moment of initial exposure to the environment of use.

A "targeted release dosage form" generally refers to an oral dosage form that is designed to deliver an API to a particular portion of the gastrointestinal tract of a subject. An exemplary targeted dosage form is an enteric dosage form that delivers a drug into the middle to lower intestinal tract but not into the stomach or mouth of the subject. Other targeted dosage forms can be delivered to other sections of the gastrointestinal tract such as the stomach, jejunum, ileum, duodenum, cecum, large intestine, small intestine, colon, or rectum.

By "delayed release" is meant that initial release of an API occurs after expiration of an approximate delay (or lag) period. For example, if release of an API from an extended-release composition is delayed two hours, then release of the API begins at about two hours after administration of the composition, or dosage form, to a subject. In general, a delayed release is opposite of an immediate release, wherein release of an API begins after no more than a few minutes after administration. Accordingly, the API release profile from a particular composition can be a delayed-extended release or a delayed-rapid release. A "delayed-extended" release profile is one wherein extended release of an API begins after expiration of an initial delay period. A "delayed-rapid" release profile is one wherein rapid release of an API begins after expiration of an initial delay period.

A "pulsatile release dosage form" is one that provides pulses of high API concentration, interspersed with low concentration troughs. A pulsatile profile containing two peaks may be described as "bimodal." A pulsatile profile of more than two peaks may be described as multi-modal.

A "pseudo-first order release profile" is one that approximates a first order release profile. A first order release profile characterizes the release profile of a dosage form that releases a constant percentage of an initial API charge per unit time.

A "pseudo-zero order release profile" is one that approximates a zero-order release profile. A zero-order release profile characterizes the release profile of a dosage form that releases a constant amount of API per unit time.

The term "adverse event" refers to any untoward medical occurrence associated with the use of a drug in humans, whether or not considered drug related.

The term "serious adverse event" refers to death, a life-threatening adverse event, inpatient hospitalization or prolongation of existing hospitalization, a persistent or significant incapacity or substantial disruption of the ability to conduct normal life functions, or a congenital anomaly/birth defect. Important medical events that may not result in death, be life-threatening, or require hospitalization may be considered serious when, such medical events include allergic bronchospasm requiring intensive treatment in an emergency room or at home, blood dyscrasias or convulsions that do not result in inpatient hospitalization, or the development of drug dependency or drug abuse, etc.

The term "regimen" refers to a course of medical treatment over a period of time. The regimen described herein includes one or more sub-regimens, such as a first regimen, a second regime, and so on, that make up the entire regimen of medical treatment. The period of time for treatment may be one or more days, one or more weeks, one or more months, etc., wherein the period of time may be repeated in a cyclic fashion one or more times. The period of time may be 28 days, defining the length of a cycle that may be repeated. A regimen may be a 28-day cycle where a compound A is administered on specific days of the cycle, defining a first regimen, and where compound B is administered on other specific days of the cycle that define a second regimen, which in total defines the entire regimen.

One example of a dosing regimen is a 28-day cycle where a compound (e.g., the composition comprising a compound of formula I) is dosed once per day on days 1 to 21 of the cycle (followed by days 22 to 28 without any dosing with the particular compound, although days 22-28 can include or exclude dosing of a second drug on a different regimen). A further example of a dosing regimen is a 28-day cycle where a compound (e.g., the composition comprising a compound of formula I) is dosed once per day on days 1 to 5, 8 to 12, and 15 to 19 of the cycle. Yet another example dosing regimen is a 28-day cycle where a compound (e.g., the composition comprising a compound of formula I) is dosed once per day on days 1, 8, and 15 of the cycle.

For combination therapy (i.e., therapy with two or more drugs), the dosing regimens can be the same for each drug, or one drug can follow one regimen and the second drug can follow a different regimen. For example, one suitable dosing regimen is a 28-day cycle where compound A (e.g., the composition comprising a compound of formula I) is dosed once per day on days 1 to 21 of the 28-day cycle, and compound B (a different anticancer drug) is dosed once per day on days 1, 8, and 15 of the 28-day cycle.

Thermokinetic Compounding.

In certain embodiments, the pharmaceutical formulations of the present disclosure are processed in a thermokinetic chamber as disclosed in U.S. Pat. No. 8,486,423 (Brough et al.), which is incorporated herein by reference. Other useful information and techniques are described by U.S. Pat. No. 10,265,301 (Miller et al.) and PCT Publication No. WO 2015/175505 (Miller et al.), and US Publication No. 2020/0009060 (Miller), which describes (in Example 1) the method to prepare the triptolide tablet described herein. These documents, incorporated herein by reference, describe the appropriate methods for blending heat sensitive or thermolabile components in a thermokinetic mixer by using multiple speeds during a single, rotationally continuous operation on a batch containing thermolabile components in order to minimize any substantial thermal degradation, so that the resulting pharmaceutical compositions have increased bioavailability and stability.

In a thermokinetic compounding (TKC) chamber the average temperature inside the chamber is ramped up to a pre-defined final temperature over the duration of processing to achieve thermokinetic compounding of an API and the one or more pharmaceutically acceptable excipients, adjuvants, additional APIs, or combinations thereof, into a composite. The length of processing and exposure to elevated temperatures during thermokinetic compounding will generally be below the thermal sensitivity threshold of the API, the excipients, the adjuvants, the additional APIs, or all of these. Multiple speeds may be used during a single, rotationally continuous TKC operation to achieve optimal thermokinetic mixing of the API and the one or more pharmaceutically acceptable excipients, adjuvants and additional APIs, or combinations thereof, into a composite with minimal thermal degradation. The pre-defined final temperature and speed(s) are selected to reduce the possibility that the API, excipients, adjuvants, additional APIs and/or processing agents are degraded or their functionality is impaired during processing. Generally, the pre-defined final temperature, pressure, time of processing and other environmental conditions (e.g., pH, moisture, buffers, ionic strength, $O_2$) will be selected to substantially eliminate API, excipient, adjuvant, additional APIs and/or processing agent degradation.

The methods described herein therefore include:

producing solid dispersions of triptolide, with or without additional APIs, by processing at low temperatures for very brief durations;

producing solid dispersions of triptolide, with or without additional APIs, in thermolabile polymers and excipients by processing at low temperatures for very brief durations;

rendering triptolide, with or without additional APIs, amorphous while dispersing in a polymeric, non-polymeric, or combination excipient carrier system;

rendering triptolide, with or without additional APIs, amorphous while dispersing in a polymeric, non-polymeric, or combination excipient carrier system and adjuvants; and producing composites comprising triptolide, with or without additional APIs, and one or more thermolabile polymers without the use of processing agents.

Additionally, compositions of the present disclosure may be processed using any technique known to one skilled in the art to produce a solid formulation, including fusion or solvent based techniques. Specific examples of these techniques include extrusion, melt extrusion, hot-melt extrusion, spray congealing, spray drying, hot-spin mixing, ultrasonic compaction, and electrostatic spinning.

Delivery.

A variety of administration routes are available for delivering-triptolide to a patient in need. The particular route selected will depend upon the particular drug selected, the weight and age of the patient, and the dosage required for therapeutic effect. The pharmaceutical compositions may conveniently be presented in unit dosage form. Triptolide suitable for use in accordance with the present disclosure, and its pharmaceutically acceptable salts, derivatives, analogs, prodrugs, and solvates thereof, can be administered alone, but will generally be administered in admixture with a suitable pharmaceutical excipient, adjuvant, diluent, or carrier selected with regard to the intended route of administration and standard pharmaceutical practice, and can in certain instances be administered with one or more additional API(s), optionally in the same unit dosage form.

Triptolide may be used in a variety of application modalities, including oral delivery as tablets, capsules or suspensions; pulmonary and nasal delivery; topical delivery as emulsions, ointments or creams; transdermal delivery; and parenteral delivery as suspensions, microemulsions or depot. As used herein, the term "parenteral" includes subcutaneous, intravenous, intramuscular, or infusion routes of administration.

Excipients.

The excipients and adjuvants that may be used in the presently disclosed compositions and composites, while potentially having some activity in their own right, for example, antioxidants, are generally defined for this application as compounds that enhance the efficiency and/or efficacy of triptolide. It is also possible to have more than one API in a given solution, so that the particles formed contain more than one API.

Any pharmaceutically acceptable excipient known to those of skill in the art may be used to produce the composites and compositions disclosed herein. Examples of excipients for use with the present disclosure include, but are not limited to, e.g., a pharmaceutically acceptable polymer, a thermolabile polymeric excipient, or a non-polymeric excipient. Other non-limiting examples of excipients include, lactose, glucose, starch, calcium carbonate, kaoline, crystalline cellulose, silicic acid, water, simple syrup, glucose solution, starch solution, gelatin solution, carboxymethyl cellulose, shellac, methyl cellulose, polyvinyl pyrrolidone, dried starch, sodium alginate, powdered agar, calcium carmelose, a mixture of starch and lactose, sucrose, butter, hydrogenated oil, a mixture of a quaternary ammonium base and sodium lauryl sulfate, glycerine and starch, lactose, bentonite, colloidal silicic acid, talc, stearates, and polyethylene glycol, sorbitan esters, polyoxyethylene sorbitan fatty acid esters, polyoxyethylene alkyl ethers, poloxamers (polyethylene-polypropylene glycol block copolymers), sucrose esters, sodium lauryl sulfate, oleic acid, lauric acid, vitamin E TPGS, polyoxyethylated glycolysed glycerides, dipalmitoyl phosphaditylcholine, glycolic acid and salts, deoxycholic acid and salts, sodium fusidate, cyclodextrins, polyethylene glycols, polyglycolyzed glycerides, polyvinyl alcohols, polyacrylates, polymethacrylates, polyvinylpyrrolidones, phosphatidyl choline derivatives, cellulose derivatives, biocompatible polymers selected from poly (lactides), poly(glycolides), poly(lactide-co-glycolides), poly(lactic acid)s, poly(glycolic acid)s, poly(lactic acid-co-glycolic acid)s and blends, combinations, and copolymers thereof.

Excipients and adjuvants may be used to enhance the efficacy and efficiency of the API. Additional non-limiting examples of compounds that can be included are binders, carriers, cryoprotectants, lyoprotectants, surfactants, fillers, stabilizers, polymers, protease inhibitors, antioxidants, bioavailability enhancers and absorption enhancers. The excipients may be chosen to modify the intended function of the active ingredient by improving flow, or bioavailability, or to control or delay the release of the API. Specific nonlimiting examples include: sucrose, trehaolose, Span 80, Span 20, Tween 80, Brij 35, Brij 98, Pluronic, sucroester 7, sucroester 11, sucroester 15, sodium lauryl sulfate (SLS, sodium dodecyl sulfate. SDS), dioctyl sodium sulphosuccinate (DSS, DOSS, dioctyl docusate sodium), oleic acid, laureth-9, laureth-8, lauric acid, vitamin E TPGS, Cremophor®EL, Cremophor® RH, Gelucire® 50/13, Gelucire® 53/10, Gelucire® 44/14, Labrafil®, Solutol® HS, dipalmitoyl phosphadityl choline, glycolic acid and salts, deoxycholic acid and salts, sodium fusidate, cyclodextrins, polyethylene glycols, Labrasol®, polyvinyl alcohols, polyvinyl pyrrolidones and tyloxapol. Using the process of the present disclosure, the morphology of the active ingredients can be modified, resulting in highly porous microparticles and nanoparticles.

Exemplary polymer carriers or thermal binders that may be used in the presently disclosed compositions and composites include but are not limited to polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; polysaccharides such as tragacanth, gum arabic, guar gum, and xanthan gum. One embodiment of the binder is poly(ethylene oxide) (PEO), which can be purchased commercially from companies such as the Dow Chemical Company, which markets PEO under the POLY OX® exemplary grades of which can include WSR N80 having an average molecular weight of about 200,000; 1,000,000; and 2,000,000.

Suitable polymer carriers or thermal binders that may or may not require a plasticizer include, for example, Eudragit® RS PO, Eudragit® S100, Kollidon® SR (poly (vinyl acetate)-co-poly(vinylpyrrolidone) copolymer), Ethocel® (ethylcellulose), HPC (hydroxypropylcellulose), cellulose acetate butyrate, poly(vinylpyrrolidone) (PVP), poly (ethylene glycol) (PEG), poly(ethylene oxide) (PEO), poly (vinyl alcohol) (PVA), hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.), cellulose acetate phthalate (CAP), cellulose acetate trimelletate (CAT), poly(vinyl acetate) phthalate (PVAP), hydroxypropylmethylcellulose phthalate (HPMCP), poly(methacrylate ethylacrylate) (1:1) copolymer (MA-EA), poly(methacrylate methylmethacrylate) (1:1) copolymer (MA-MMA), poly (methacrylate methylmethacrylate) (1:2) copolymer, Eudragit® L-30-D (MA-EA, 1:1), Eudragit® L100-55 (MA-EA, 1:1), Eudragit® EPO (poly(butyl methacylate-co- (2-dimethylaminoethyl) methacrylate-co-methyl methacrylate) 1:2:1), hydroxypropylmethylcellulose acetate succinate (HPMCAS), Coateric® (PVAP), Aquateric® (CAP), and AQUACOAT® (HPMCAS), Soluplus® (polyvinyl caprolactam-polyvinyl acetate-polyethylene glycol graft copolymer, BASF), Luvitec® K 30 (polyvinylpyrrolidone, PVP), Kollidon® (polyvinylpyrrolidone, PVP), polycaprolactone, starches, pectins; polysaccharides such as tragacanth, gum arabic, guar gum, and xanthan gum.

The carrier may also contain various functional excipients, such as: hydrophilic polymer, antioxidant, super-disintegrant, surfactant including amphiphilic molecules, wetting agent, stabilizing agent, retardant, similar functional excipient, or combination thereof, and plasticizers including citrate esters, polyethylene glycols, PG, triacetin, diethylphthalate, castor oil, and others known to those or ordinary skill in the art. Extruded material may also include an acidifying agent, adsorbent, alkalizing agent, buffering agent, colorant, flavorant, sweetening agent, diluent, opaquant, complexing agent, fragrance, preservative or a combination thereof.

Exemplary hydrophilic polymers which can be a primary or secondary polymeric carrier that can be included in the composites or composition disclosed herein include poly (vinyl alcohol) (PVA), polyethylene-polypropylene glycol (e.g., POLOXAMER®), carbomer, polycarbophil, or chitosan. Hydrophilic polymers for use with the present disclosure may also include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan, and povidone. Hydrophilic polymers also include polyethylene oxide, sodium carboxymethycellulose, hydroxyethyl methyl cellulose, hydroxymethyl cellulose, carboxypolymethylene, polyethylene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

Compositions with enhanced solubility may comprise a mixture of triptolide and an additive that enhances the solubility of the triptolide. Examples of such additives include but are not limited to surfactants, polymer carriers, pharmaceutical carriers, thermal binders or other excipients. A particular example may be a mixture of triptolide with a surfactant or surfactants, triptolide with a polymer or polymers, or triptolide with a combination of a surfactant and polymer carrier or surfactants and polymer carriers. A further example is a composition where the triptolide is a derivative or analog thereof.

Examples of surfactants that can be used to enhance solubility include but are not limited to sodium dodecyl sulfate, dioctyl docusate sodium, Tween 80, Span 20, Cremophor® EL or Vitamin E TPGS. Examples of polymer carriers that can be used to enhance solubility include but are not limited to Soluplus®, Eudragit® L100-55, Eudragit® EPO, Kollidon® VA 64, Luvitec®. K 30, Kollidon®, AQOAT®-HF, and AQOAT®-LF. The composition of the present disclosure can thus be any combination of one or more of the APIs, zero, one or more of surfactants or zero, one or more of polymers presented herein.

Solubility can be indicated by peak solubility, which is the highest concentration reached of a species of interest over time during a solubility experiment conducted in a specified medium. The enhanced solubility can be represented as the ratio of peak solubility of the agent in a pharmaceutical composition of the present disclosure compared to peak solubility of the reference standard agent under the same conditions. Preferable, an aqueous buffer with a pH in the range of from about pH 4 to pH 8, about pH 5 to pH 8, about pH 6 to pH 7, about pH 6 to pH 8, or about pH 7 to pH 8, such as, for example, pH 4.0, 4.5, 5.0, 5.5, 6.0, 6.2, 6.4, 6.6, 6.7, 6.8, 6.9, 7.0, 7.1, 7.2, 7.4, 7.6, 7.8, or 8.0, may be used for determining peak solubility. This peak solubility ratio can be about 2:1, 3:1, 4:1, 5:1, 6:1, 7:1, 8:1, 9:1, 10:1, 12:1, 15:1, 20:1, 25:1, 30:1, 35:1, 40:1, 45:1, 50:1, 55:1 or higher.

Bioavailability can be indicated by the AUC of triptolide as determined during in vivo testing, where AUC is the area under the blood concentration versus time curve for triptolide. Enhanced bioavailability can be represented as the ratio of AUC of the triptolide in a pharmaceutical composition of the present disclosure compared to AUC of the reference standard triptolide under the same conditions. This AUC ratio reflecting enhanced bioavailability can be about 4:3, 5:3, 2:1, 5:1, 6:1, 7:1, 8:1, 9:1, 10:1, 12:1, 15:1, 20:1, 25:1, 30:1, 35:1, 40:1, 45:1, 50:1, 55:1, 60:1, 65:1, 70:1, 75:1, 80:1, 85:1, 90:1, 95:1, 98:1, 99:1, 100:1 or higher.

Further Detailed Description of the Invention

Triptolide is a diterpenoid tri-epoxide compound inhibiting cell growth and exhibiting preclinical antitumor activity. However, a major limitation of triptolide's clinical utility is its low solubility.

Thus, in accordance with the present disclosure, there is provided a method of making a pharmaceutical composition comprising (a) providing pure amorphous and/or crystalline triptolide and one or more pharmaceutically acceptable excipients; (b) compounding the materials of step (a) in a thermokinetic mixer at less than or equal to 200° C. for less than about 300 seconds, wherein the thermokinetic compounding of the triptolide and the one or more pharmaceutically acceptable excipients forms a melt blended pharmaceutical composite. The one or more pharmaceutically acceptable excipients may comprise one or more polymers, a processing agent, and/or a surfactant.

Step (b) may comprise compounding the materials of step (a) in a thermokinetic mixer for less than about 240 seconds, less than about 180 seconds, less than about 120 second, less than about 90 seconds, less than about 60 seconds, or less than about 30 seconds. Step (b) may be performed at a temperature of about 100° C., about 125° C., about 150° C., about 180° C., or about 100° C. to 200° C.

The composition may remain amorphous per x-ray diffraction analysis following storage in an open container at about 40° C., relative humidity of about 75%, at five weeks. The composition may have a single glass transition temperature.

The one or more pharmaceutically acceptable excipients may comprise a pharmaceutical polymer, a surfactant, or one or more surfactants and one or more polymer carriers. The composite may be an amorphous dispersion. The pharmaceutical polymer may comprise an agent selected from sodium carboxymethyl-cellulose (croscarmellose sodium), poly(vinyl acetate)-co-poly(vinylpyrrolidone) copolymer, ethylcellulose, hydroxypropylcellulose, cellulose acetate butyrate, poly(vinylpyrrolidone), poly(ethylene glycol), poly(ethylene oxide), poly(vinyl alcohol), hydroxypropyl methylcellulose, hydroxyethylcellulose, dimethylaminoethyl methacrylate-methacrylic acid ester copolymer, ethylacrylate-methylmethacrylate copolymer, cellulose acetate phthalate, cellulose acetate trimelletate, poly(vinyl acetate) phthalate, hydroxypropylmethylcellulose phthalate, poly (methacrylate ethylacrylate) (1:1) copolymer, poly(methacrylate methylmethacrylate) (1:1) copolymer, poly(methacrylate methylmethacrylate) (1:2) copolymer, hydroxypropylmethylcellulose acetate succinate and polyvinyl caprolactam-polyvinyl acetate-polyethylene glycol graft copolymer.

The triptolide to pharmaceutical polymer ratio may be about 1:1 to about 1:20, or about 1:1 to about 1:10, including about 1:5, about 1:6, about 1:7, about 1:8, or about 1:9.

In further embodiments, the formulation can include one or more polymer excipients selected from hypromellose acetate succinate (HPMCAS-LMP, HPMCAS-MMP, or HPMCAS-HMP), methacrylic acid-ethyl acrylate copolymer excipient (e.g., Kollicoat MAE L100-55 and/or L100), hydroxypropyl methylcellulose (HPMC), copovidone, and polyvinylpyrrolidone (PVP; K30 or K12) in combination with a 1% to 50% drug load, often approximately a 1-2% drug load.

One or more surfactants (optional components) may comprise an agent selected from sodium dodecyl sulfate, dioctyl sodium sulphosuccinate, polyoxyethylene (20) sorbitan monooleate, glycerol polyethylene glycol oxystearate-fatty acid glycerol polyglycol esters-polyethylene glycols-glycerol ethoxylate, glycerol-polyethylene glycol ricinoleate-fatty acid esters of polyethyleneglycol-polyethylene glycols-ethoxylated glycerol, vitamin E TPGS and sorbitan laurate.

In certain embodiments, the surfactant comprises an agent selected from sodium dodecyl sulfate, dioctyl sodium sulphosuccinate, polyoxyethylene (20) sorbitan monooleate, glycerol polyethylene glycol oxystearate-fatty acid glycerol polyglycol esters-polyethylene glycols-glycerol ethoxylate, glycerol-polyethylene glycol ricinoleate-fatty acid esters of polyethyleneglycol-polyethylene glycols-ethoxylated glycerol, vitamin E TPGS, and sorbitan laurate, and the pharmaceutical polymer comprises an agent selected from sodium carboxymethyl-cellulose, poly(vinyl acetate)-co-poly(vinylpyrrolidone) copolymer, ethylcellulose, hydroxypropylcellulose, cellulose acetate butyrate, poly(vinylpyrrolidone), poly(ethylene glycol), poly(ethylene oxide), poly (vinyl alcohol), hydroxypropyl methylcellulose, hydroxyethylcellulose, dimethylaminoethyl methacrylate-methacrylic acid ester copolymer, ethylacrylate-methylmethacrylate copolymer, cellulose acetate phthalate, cellulose acetate trimelletate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropylmethylcellulose acetate succinate and polyvinyl caprolactam-polyvinyl acetate-polyethylene glycol graft copolymer.

The one or more pharmaceutically acceptable excipients may comprise a processing agent, which may be a plasticizer. Alternatively, the composition may exclude a processing agent/plasticizer.

The one or more pharmaceutically acceptable excipients can comprise a water-soluble pharmaceutical polymer, such as a water soluble polymer selected from hydroxypropylmethylcellulose acetate succinate, poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropyl methylcellulose, poly(vinyl alcohol), and polyvinyl caprolactam-polyvinyl acetate-polyethylene glycol graft copolymer.

The one or more pharmaceutically acceptable excipients may comprise a cross-linked pharmaceutical polymer, such as carbomer, crospovidone, or croscarmellose sodium. The one or more pharmaceutically acceptable excipients may also comprise a pharmaceutical polymer of high melt viscosity. The one or more pharmaceutically acceptable excipients may comprise a thermally labile pharmaceutical polymer. The one or more pharmaceutically acceptable excipients may comprise poly(methacrylate ethylacrylate) (1:1) copolymer or poly(vinyl acetate)-co-poly(vinylpyrrolidone), or the one or more pharmaceutically acceptable excipients may comprise poly(methacrylate ethylacrylate) (1:1) copolymer and poly(vinyl acetate)-co-poly(vinylpyrrolidone). The one or more pharmaceutically acceptable excipients may also comprise poly(vinyl acetate)-co-poly (vinylpyrrolidone) and/or hydroxypropylmethylcellulose acetate succinate.

The composition may comprise about 0.1-50% triptolide, about 0.5-20% triptolide, about 1-10% triptolide, about 0.5% triptolide, 1% triptolide, 1.5% triptolide, 2% triptolide, 2.5% triptolide, 3% triptolide, 3.5% triptolide, 4% triptolide, or 5% triptolide. Accordingly, the pharmaceutical composition may comprise about 0.1 mg triptolide, about 0.25 mg triptolide, about 0.5 mg triptolide, about 1 mg triptolide, about 1.5 mg triptolide, about 2 mg triptolide, about 2.5 mg triptolide, about 5 mg triptolide, about 9 mg triptolide, about 10 mg triptolide, about 12.5 mg triptolide, about 25 mg triptolide, about 36 mg triptolide, or about 50 mg triptolide, or a range from one to a second of the aforementioned values.

The purity of triptolide used in the composition may be about 95%, about 99%, about 99.5%, or about 95% to about 100%. The purity of the composition may be about 95%, about 99%, about 99.5%, or about 95% to about 100%. The composition may have less than about 1.0% degradation products of triptolide.

The pharmaceutical composition may comprise a second active pharmaceutical ingredient in addition to triptolide, such as wherein the second active pharmaceutical ingredient is an anticancer agent.

The pharmaceutical composition may exhibit a peak solubility of the triptolide in the composition of greater than 4-6 pg/mL, in an aqueous buffer with a pH range of 4 to 8, such as 4, 4.25, 4.50, 4.75, 5, 5.25, 5.50, 5.75 or 6 μg/mL. The peak solubility of the triptolide and the reference standard triptolide after an 8 hour dissolution test in an aqueous buffer with a pH range of 4 to 8 may have a ratio of greater than 4:1. The AUC of the triptolide in the composition and AUC of the reference standard triptolide may have a ratio that is greater than 4:3, such as 5:3, 2:1, 7:3 and 4:1. The pharmaceutical composition may have at least about 97% drug potency of triptolide as compared to the unprocessed triptolide.

The pharmaceutical composition may be formulated as an oral dosage form, such as a tablet, a capsule, or a sachet, wherein the tablet may be a round flat tablet, a round concave tablet, an elongated tablet, or a minitab. The oral dosage form may be an extended-release form or an immediate release form. The oral dosage form can be a disintegrating tablet or an eroding tablet.

Also provided is pharmaceutical composition produced by a process comprising the steps of (a) providing crystalline or amorphous triptolide and one or more pharmaceutically acceptable excipients; (b) compounding the materials of step (a) in a thermokinetic mixer for less than about 300 seconds and at less than or equal to about 200° C., wherein the thermokinetic compounding of triptolide and the one or more pharmaceutically acceptable excipients forms a melt blended pharmaceutical composition (process described above).

The resulting composition may be a nanocomposite or may be a partially or wholly amorphous dispersion. The pharmaceutical composition may remain amorphous per x-ray diffraction analysis following storage in an open container at about 40° C., relative humidity of about 75%, at five weeks. The composition may have a single glass transition temperature. The pharmaceutical composition may be co-processed with second active pharmaceutical ingredient, such as wherein the second active pharmaceutical ingredient is an anticancer agent.

In addition, the invention provides a pharmaceutical composition comprising an amorphous dispersion of triptolide and one or more pharmaceutically acceptable excipients thermally processed into a composite, wherein the composite has less than about 1.0% degradation products of triptolide. In typical embodiments, the pharmaceutical composition has less than about 0.5% degradation products of triptolide, less than about 0.25% degradation products of triptolide, or less than about 0.1% degradation products of triptolide. The pharmaceutical composition may exclude a processing agent or plasticizer.

The one or more pharmaceutically acceptable excipients may include one or more water soluble pharmaceutical polymers such as hydroxypropylmethylcellulose acetate succinate, cellulose, poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropyl methylcellulose, poly(vinyl alcohol), or polyvinyl caprolactam-polyvinyl acetate-polyethylene glycol graft copolymer. The triptolide to water soluble pharmaceutical polymer ratio may be about 1:2 to about 1:50, 1:10 to about 1:45, 1:30 to about 1:40, or 1:35 to about 1:40, for example, for each water soluble pharmaceutical polymer.

In further embodiments, the invention provides:

- a pharmaceutical composition comprising an amorphous dispersion of triptolide and one or more pharmaceutically acceptable excipients thermally processed into a composite, wherein the composition which does not have substantial degradation of triptolide and each excipient;
- a pharmaceutical composition comprising an amorphous dispersion of triptolide and one or more pharmaceutically acceptable excipients thermally processed into a composite, wherein the composition which has less than about 1.0% degradation products of triptolide, does not have substantial degradation of each excipient, and the composition does not comprise a processing agent;
- a pharmaceutical composition comprising an amorphous dispersion of triptolide and one or more pharmaceutically acceptable excipients thermally processed into a composite, wherein the composition which has less than about 1.0% degradation products of triptolide, and the composition does not comprise a processing agent;
- a pharmaceutical composition comprising an amorphous dispersion of triptolide and one or more pharmaceutically acceptable excipients thermally processed into a composite, in which the composite exhibits a single glass transition temperature, and which does not have substantial degradation of triptolide, while a formulation of triptolide and identical pharmaceutically acceptable excipients processed thermally by a process other than thermokinetic compounding exhibits two or more glass transition temperatures; and
- a pharmaceutical composition comprising an amorphous dispersion of triptolide and one or more pharmaceutically acceptable excipients thermally processed into a composite, in which the glass transition temperature is significantly higher than the glass transition temperature of a formulation of triptolide and identical pharmaceutically acceptable excipients processed thermally by a process other than thermokinetic compounding, and which does not have substantial degradation of triptolide, and wherein the composition does not comprise a processing agent.

The pharmaceutical composition of any of the preceding embodiments can have at least about 97% drug potency of triptolide as compared to the unprocessed triptolide.

In addition, novel pharmaceutical compositions or composites discussed above may be further processed according to methods well known to those of skill in the art, including but not limited to compression molding, tablet compression, capsule filling, film-coating, or injection molding into a final product. In certain embodiments, the composite can be the final product. Another embodiment is directed to addition of triptolide and one or more pharmaceutically acceptable excipients in a ratio of about 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, or 1:10. Yet another embodiment is directed to addition of triptolide and one or more pharmaceutically acceptable adjuvants in a ratio of about 1:2, 1:2.5, 1:3, 1:3.5, 1:4, 1:4.5, 1:5, 1:5.5, 1:6, 1:6.5, 1:7, 1:7.5, 1:8, 1:8.5, 1:9, 1:9.5, 1:10, 1:15, 1:20 1:25, 1:30, 1:40, 1:50, 1:60, 1:70, 1:80, 1:90, 1:100, 1:150, 1:200, 1:300, 1:400 or 1:500. An additional embodiment is directed to addition of triptolide and one or more additional active pharmaceutical ingredient ("API") to the composition. The ratio of triptolide to other API may be approximately 20:1, 16:1, 6:1, 2:1, 1:1, 1:2, 1:6, 1:16, 1:20.

The thermokinetic processing may be conducted in a thermokinetic chamber. A thermokinetic chamber can be an enclosed vessel or chamber in which thermokinetic compounding (TKC) occurs. In one aspect, the average temperature inside the chamber is ramped up to a pre-defined final temperature over the duration of processing to achieve optimal thermokinetic mixing of triptolide and the one or more pharmaceutically acceptable excipients, adjuvants, additional APIs, or any combination thereof, into a composite. In another aspect, multiple speeds are used during a single, rotationally continuous TKC operation to achieve optimal thermokinetic mixing of triptolide and one or more pharmaceutically acceptable excipients, adjuvants, additional APIs, or any combination thereof, into a composite with minimal thermal degradation. The length of processing and exposure to elevated temperatures or speeds during thermokinetic mixing will generally be below the thermal sensitivity threshold of triptolide, excipient(s), adjuvant(s), or additional API(s). In another aspect, the thermokinetic processing is performed at an average temperature at or below the melting point of triptolide, excipient(s), adjuvant(s), or additional API(s); the thermokinetic processing is performed at an average temperature at or below the glass transition temperature of triptolide, excipient(s), adjuvant(s), or additional API(s); or the thermokinetic processing is performed at an average temperature at or below the molten transition point of triptolide, excipient(s), adjuvant(s), or additional API(s).

In certain embodiments, the thermokinetic processing substantially eliminates triptolide, excipient, adjuvant or additional API degradation. For example, TKC may generate compositions and composites with less than about 2.0%, 1.0%, 0.75%, 0.5%, 0.1%, 0.05%, or 0.01% degradation products of triptolide, adjuvant, excipient or additional API. In other embodiments, TKC may generate compositions with a minimum of at least about 90%, 91%, 92%, 93%, 94%, 95%, 96%, 97%, 98%, 99%, or 99.9% drug potency with respect to triptolide. Examples of TKC may be performed for less than 5, 10, 15, 20, 25, 30, 35, 40, 45, 50, 55, 60, 75, 100, 120, 150, 180, 240 and 300 seconds. Generally, TKC may be performed for less than 5, 10, 15, 20, 25, 30, 35, 40, 45, 50, 55, 60, 75, 100, 120, 150, 180, 240 and 300 seconds, and any ranges therein. In certain embodiments, the triptolide has an amorphous morphology.

In certain embodiments, the formulations may provide for enhanced solubility of triptolide through the mixing of triptolide with pharmaceutically acceptable polymers, carriers, surfactants, excipients, adjuvants or any combination thereof. Thus, for example, compositions which display enhanced solubility are comprised of triptolide and a surfactant or surfactants, triptolide and a pharmaceutical carrier (thermal binder) or carriers, or triptolide and a combination of a surfactant and pharmaceutical carrier or surfactants and carriers.

A further embodiment of the present disclosure is a pharmaceutical composition comprising triptolide and one or more pharmaceutically acceptable excipients, adjuvants, additional APIs, or a combination thereof, wherein greater than about 80% of the dose is dissolved within two hours after a media change from aqueous media of about pH 1.2 to an aqueous buffer of pH between 4 and 8.

A further embodiment of the present disclosure is a pharmaceutical composition comprising triptolide and one or more pharmaceutically acceptable excipients, adjuvants, additional APIs, or a combination thereof, wherein a ratio of peak solubility of triptolide in the composition over peak solubility of the reference standard triptolide, is greater than about 2:1, 3:1, about 4:1, about 5:1, about 6:1, about 7:1, about 8:1, about 9:1, or about 10:1.

A further embodiment of the present disclosure is a pharmaceutical composition comprising triptolide and one or more pharmaceutically acceptable excipients, adjuvants, or additional APIs, wherein AUC of the triptolide in the composition and AUC of the reference standard triptolide, when delivered orally have a ratio that is greater than about 4:3, 5:3, 2:1, or about 5:1.

A further embodiment of the present disclosure is a method of formulating a pharmaceutical composition comprising triptolide and one or more pharmaceutically acceptable excipients, adjuvants, additional APIs, or any combination thereof, by TKC to increase bioavailability of the triptolide, comprising thermokinetic processing of the triptolide with the one or more pharmaceutically acceptable excipients, adjuvants, additional APIs, or any combination thereof until melt blended into a composite.

A further embodiment of the present disclosure is a pharmaceutical composition comprising triptolide and one or more pharmaceutically acceptable excipients, adjuvants, additional APIs, or any combination thereof, wherein the composition is a homogenous, heterogenous, or heterogeneously homogenous composition which has a single glass transition temperature.

A further embodiment of the present disclosure is a pharmaceutical composition comprising triptolide and one or more pharmaceutically acceptable excipients, adjuvants, additional APIs, or any combination thereof, processed into a composite, wherein the composite is a homogenous, heterogenous, or heterogeneously homogenous composition which has less than about 1.0%, less than about 2%, less than about 3%, or less than about 4% degradation products of the triptolide.

A further embodiment of the present disclosure is particle size reduction of triptolide in an excipient carrier system in which triptolide is not miscible, not compatible, or not miscible or compatible. Particle size reduction can be achieved by attrition of the API particles according to the mechanical forces imparted by the TKC process with simultaneous mixing with the molten excipient carrier. Particle size reduction can also be achieved by melting triptolide with the carrier at elevated temperature by TKC processing and subsequently forcing recrystallization of triptolide as fine particles in the carrier upon quenching. By this method, a secondary annealing step may also be required to bring the recrystallization process to completion. In one aspect, triptolide is in the form of a nanocomposite with the excipient carrier system.

The novel pharmaceutical compositions or composites made by TKC and disclosed herein may be administered to a treat a mammal, including without limitation a human patient or subject, to treat cancer. In certain embodiments, such compositions or composites may be used in a method of treating a subject who experiences a suboptimal or inadequate response to maximum approved doses of currently available triptolide formulations. Such suboptimal or inadequate response may result in such subjects not achieving a sufficient therapeutic response. Subjects that may be treated by such compositions or composites include children, juveniles, young adults and adults of any age. In particular embodiments, the bioavailability of such compositions or composites are independent of a food effect. For example, the bioavailable of such compositions or composites are independent of any consumption by a subject of a high fat meal prior to, with, or shortly after administration of such compositions or composites. The administration of the pharmaceutical composition to the mammal may result in an AUC value that is statistically equivalent regardless of whether the subject has fasted or has consumed a high fat meal immediately prior to administration of the composition.

Also provided are pharmaceutical compositions comprising an amorphous dispersion of triptolide and one or more pharmaceutically acceptable excipients thermally processed into a composite by thermokinetic compounding, in which the composite is a single phase, amorphous composite, wherein at least one of the pharmaceutically acceptable excipients is immiscible with triptolide when thermally processed by a process other than thermokinetic compounding.

In particular, there is provided a method of treating a subject for cancer in a subject who experiences a suboptimal or inadequate response to non-amorphous dispersions or crystalline forms of triptolide comprising administering to the subject a pharmaceutical composition comprising an amorphous dispersion of triptolide and one or more pharmaceutically acceptable excipients. The amorphous dispersion of triptolide may be thermally processed into a composite by thermokinetic compounding, and the non-amorphous dispersion or crystalline form of triptolide may be thermally processed by a process other than thermokinetic compounding. The subject may have a type of cancer as recited herein. The bioavailability of the amorphous dispersion of triptolide may be independent of any food effect, such as a food effect from consuming a high fat meal.

Still further there is provided a pharmaceutical composition comprising triptolide and one or more pharmaceutically acceptable excipients thermally processed into a composite by thermokinetic compounding, wherein administration of the composition to fasted human subjects provides an $AUC_{0-T}$ value is at least 15% greater when compared to administration of a pharmaceutical composition comprising triptolide and one or more pharmaceutically acceptable excipients thermally processed by a process other than thermokinetic compounding. The $AUC_{0-T}$ value may be at least 25% greater.

Also provided is a pharmaceutical composition comprising triptolide and one or more pharmaceutically acceptable excipients thermally processed into a composite by thermokinetic compounding, wherein administration of the composition to human subjects provides an AUC increase of at least 50% when compared to administration of a pharmaceutical composition comprising triptolide and one or more pharmaceutically acceptable excipients thermally processed by a process other than thermokinetic compounding.

Also provided is a pharmaceutical composition comprising triptolide and one or more pharmaceutically acceptable excipients thermally processed into a composite by thermokinetic compounding, wherein administration of the composition to fasted human subjects provides a $C_{max}$ standard deviation of less than 30% and an $AUC_{0-\infty}$ standard deviation of less than 35%.

Embodiments of the Technology

This disclosure provides a pharmaceutical composition comprising an amorphous solid dispersion of a compound formula I:

(I)

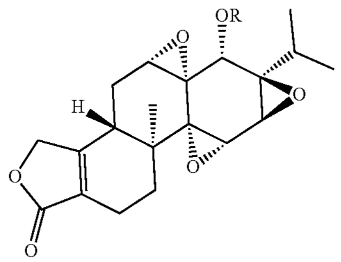

;

wherein R is H, —$CH_2O(PO_3H_2)$, or a salt of —$CH_2O(PO_3H_2)$ (e.g., a salt of —$CH_2O(PO_3X_2)$ wherein each X is independently H or a pharmaceutically acceptable cation such as sodium or potassium); and one or more pharmaceutically acceptable excipients; wherein the composition has a single glass transition temperature.

In various embodiments, the pharmaceutical composition and methods for using or making the composition can have one or more of the characteristics, properties, or components described below, optionally in combination with other characteristics, properties, or components described above in this disclosure.

In various embodiments, the compound of formula I is triptolide or minnelide (IUPAC name: disodium; [(1S,2S,4S,5S,7S,8R,9R,11S,13S)-1-methyl-17-oxo-7-propan-2-yl-3,6,10,16-tetraoxaheptacyclo[11.7.0.0$^{2,4}$.0$^{2,9}$.0$^{5,7}$.0$^{9,11}$.0$^{14,18}$]icos-14(18)-en-8-yl]oxymethyl phosphate).

In various embodiments, the cancer subject is administered about 0.25 mg to about 0.75 mg of minnelide or triptolide. In various embodiments, the cancer subject is administered a milligram amount of minnelide or triptolide that is about 0.15 mg, 0.25 mg, 0.35 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.2 mg, 2.3 mg, 2.4 mg, 2.5 mg, 2.6 mg, 2.7 mg, 2.8 mg, 2.9 mg, 3.0 mg, 3.5 mg, 4.0 mg, 4.5 mg, 5.0 mg, 5.5 mg, about 6.0 mg, or another amount recited herein.

In various embodiments, the cancer subject is administered about 200 mg/m$^2$ to about 500 mg/m$^2$ of triptolide or minnelide. In various embodiments, the cancer subject can be administered a dose of triptolide or minnelide that is about 200 mg/m$^2$, 225 mg/m$^2$, 250 mg/m$^2$, 265 mg/m$^2$, 275 mg/m$^2$, 280 mg/m$^2$, 290 mg/m$^2$, 300 mg/m$^2$, 310 mg/m$^2$, 320 mg/m$^2$, 325 mg/m$^2$, 335 mg/m$^2$, 350 mg/m$^2$, 375 mg/m$^2$, 400 mg/m$^2$, 425 mg/m$^2$, 450 mg/m$^2$, 475 mg/m$^2$, or about 500 mg/m$^2$.

In some embodiments, the cancer subject is administered about 0.25 mg of triptolide or minnelide, about 0.5 mg of triptolide or minnelide, about 0.75 mg of triptolide or minnelide, about 1 mg of triptolide or minnelide, about 1.25 mg of triptolide or minnelide, about 1.5 mg of triptolide or minnelide, or about 1.75 mg of triptolide or minnelide. In other embodiments, the cancer subject is administered about 2 mg of triptolide or minnelide, or another amount or range of amounts of triptolide or minnelide recited herein.

In general, a suitable dose will be in the range of from about 3 to about 100 μg/kg of body weight per day (e.g. from about 6 to about 96 jig/kg of body weight per day or from about 6 to about 48 μg/kg of body weight per day, or from about 6 to about 24 μg/kg of body weight per day, or from about 12 to about 24 μg/kg of body weight per day).

The triptolide or minnelide is conveniently formulated in unit dosage form; for example, containing from about 80 μg to about 8000 μg, conveniently from about 480 μg to about 7680 μg, conveniently from about 480 jig to about 3840 μg, and conveniently from about 960 μg to about 1920 μg. In one embodiment, the invention provides a composition comprising a compound of the invention formulated in such a unit dosage form.

As would be readily recognized by one of skill in the art, any specific dosage amount recited in the preceding paragraphs for triptolide and/or minnelide can be used in combination with any suitable dosage amount for the second drug.

In various embodiments, the cancer is brain cancer, gastric cancer, pancreatic cancer, ovarian cancer, breast cancer, bladder cancer, skin cancer, or a combination thereof. In some embodiments, cancer is gastric cancer. In some embodiments, the method effectively treats a cancer subject suffering from or further suffering from brain cancer, gastric cancer, pancreatic cancer, ovarian cancer, breast cancer, bladder cancer, skin cancer, or a combination thereof.

In various embodiments, the cancer subject is a human. In various embodiments, the cancer subject is a female human or a male human.

In various embodiments, the combination or composition effectively treats the cancer without causing a complete blood count of the cancer subject to lower by more than 25%, 20%, 15%, 10%, or 5% from baseline. In various embodiments, the combination or composition effectively treats the cancer without causing a platelet count or an absolute neutrophil count in the cancer subject to lower by more than 25%, 20%, 15%, 10%, or 5% from baseline.

In some embodiments, the methods described herein are used to treat a cancer that has become refractory, or to treat a cancer that is resistant or non-responsive to other methods of cancer treatment. In some embodiments, the cancer is a brain cancer, glioma, or diffuse midline glioma (DMG) that has become refractory, resistant, or non-responsive to other methods of cancer treatment.

The compositions described herein can be administered in combination with other therapeutic agents, for example, other agents that are useful for the treatment of cancer (e.g., pancreatic cancer, ovarian cancer, colorectal cancer, non-Hodgkin lymphoma, leukemia, acute and chronic myelogenous leukemia, neuroblastoma, thyroid carcinoma, osteosarcoma, breast, prostate cancer, esophageal cancer, bladder cancer, gastric carcinoma, urothelial cancer, glioblastoma multiforme, colon cancer, uterine cervical cancer, fibrosarcoma, squamous cell carcinoma, multiple myeloma, cholangiocarcinoma, non-small cell lung cancer). Examples of such agents include 5-fluorouracil, TRAIL (TNF-related apoptosis-inducing ligand), DR-4/5 activating antibodies, cyclophosphamide, hydroxydaunorubicin (doxorubicin), oncovin (vincristine), paclitaxel, doxetaxel, cisplatin, carboplatin, CPT-11, bortezimib and prednisone-prednisolone.

As would be readily recognized by one of skill in the art, the triptolide in any formulation described herein can be exchanges with minnelide or another triptolide prodrug or derivative, for example, a triptolide prodrug or derivative as recited in one or more of the documents incorporated herein by reference.

Classification of Adverse Events by Severity.

The triptolide formulations described herein can reduce the number and severity of adverse events in a patient treated with the formulation. The severity of each Adverse Event (AE) follows guidelines from the National Cancer Institute Common Terminology Criteria for Adverse Events (NCI CTCAE). A brief summary is as follows:

Grade 1: An AE that is transient or mild discomfort, not interfering with the patient's daily activity performance or functioning; medical intervention/therapy may be required.

Grade 2: An AE of sufficient severity as to possibly make the patient moderately uncomfortable; possibly influencing the patient's daily activity performance or functioning; generally, not impairing the patient's ability to continue in the study; and/or possibly needing therapeutic intervention.

Grade 3: An AE event generally causing severe discomfort, significantly influencing the patient's daily activity performance or functioning, generally requiring alteration or cessation of study drug administration, and/or generally requiring therapeutic intervention with hospitalization possible.

Grade 4: An AE that is considered to be life threatening, resulting in significant disability or incapacity, and/or representing the worst possible occurrence of that event with hospitalization probable.

Grade 5: A death related to an AE.

Combination Therapy.

A triptolide tablet as described herein can be used in combination with other anticancer agents to provide enhanced cancer therapy. In one embodiment, the triptolide tablet can be administered to a patient diagnosed with cancer in combination with the administration of paclitaxel, for example, for the treatment of gastric cancer. In another embodiment, the triptolide tablet can be administered to a patient diagnosed with cancer in combination with the administration of paclitaxel (or nab-paclitaxel) and gemcitabine, for example, for the treatment of pancreatic cancer. These combination therapies can be carried out using specific treatment regimen such as those described by International Patent Publications WO 2024/187139 (Velagapudi) and WO 2024/186320 (Velagapudi), each of which is incorporated by reference.

Gastric Cancer.

A combination therapy method for treating gastric cancer in a cancer subject comprises administering to the cancer subject, during a 28 day cycle, a therapeutically effective combination of:

a) a triptolide tablet (prepared as described herein) comprising about 0.25 mg to about 2.0 mg of triptolide according to a first regimen wherein a dose is given once per day on days 1 to 5, 8 to 12, and 15 to 19 of the cycle; and
b) about 60 $mg/m^2$ to about 80 $mg/m^2$ of paclitaxel according to a second regimen wherein a dose is given once per day on days 1, 8, and 15 of the cycle; wherein the 28-day cycle is repeated one or more times and the combination effectively treats the gastric cancer.

The cancer subject can be administered about 0.25 mg to about 1.5 mg of triptolide according to the first regimen. The amount of triptolide in the triptolide tablet can be, for example, about 0.25 mg, about 0.5 mg, about 0.75 mg, about 1 mg, about 1.25 mg, or about 1.5 mg, for the first regiment, each of which can be used in the combination therapy with about 60 $mg/m^2$ of paclitaxel, about 70 $mg/m^2$ of paclitaxel, or about 80 $mg/m^2$ of paclitaxel, for the second regimen. This combination therapy can also treat ovarian cancer, breast cancer, bladder cancer, pancreatic cancer, skin cancer, or a combination thereof, during the treatment of gastric cancer. The treatment can effectively treat the gastric cancer without causing a complete blood count of the cancer subject to lower by more than 25% from baseline, and/or without causing a platelet count or an absolute neutrophil count in the cancer subject to lower by more than 25% from baseline.

Pancreatic Cancer.

A combination therapy method for treating pancreatic cancer in a cancer subject comprises administering to the cancer patient during a 28 day cycle a therapeutically effective combination of:

a) a triptolide tablet (prepared as described herein) comprising about 0.25 mg to about 2.0 mg of triptolide according to a first regimen wherein a dose is given once per day on days 1 to 5, 8 to 12, and 15 to 19 of the cycle;
b) about 75 $mg/m^2$ to about 125 $mg/m^2$ of paclitaxel or nab-paclitaxel according to a second regimen wherein a dose is given once per day on days 1, 8, and 15 of the cycle; and
c) about 600 $mg/m^2$ to about 1000 $mg/m^2$ of gemcitabine according to the second regimen of the cycle;

wherein the cycle is repeated one or more times and the combination effectively treats the pancreatic cancer.

The cancer subject can be administered about 0.25 mg to about 1 mg of triptolide according to the first regimen. The amount of triptolide in the triptolide tablet can be, for example, about 0.25 mg, about 0.5 mg, about 0.75 mg, or about 1 mg, for the first regiment, each of which can be used in the combination therapy with about 75 $mg/m^2$ of paclitaxel (or nab-paclitaxel, throughout this description), about 100 $mg/m^2$ of paclitaxel, or about 125 $mg/m^2$ of paclitaxel, for the second regimen, wherein each combination can be used in the combination therapy with about 600 $mg/m^2$ of gemcitabine, about 800 $mg/m^2$ of gemcitabine, or about 1,000 $mg/m^2$ of gemcitabine, each according to the second regimen. This combination therapy can also treat gastric cancer, ovarian cancer, breast cancer, bladder cancer, skin cancer, or a combination thereof, during the treatment of pancreatic cancer. The treatment can effectively treat the pancreatic cancer without causing a complete blood count of the cancer subject to lower by more than 25% from baseline, and/or without causing a platelet count or an absolute neutrophil count in the cancer subject to lower by more than 25% from baseline. In some embodiments, the pancreatic cancer is metastatic adenocarcinoma of the pancreas.

Statements of Embodiments of the Technology

The technology described herein includes embodiments described by the following Statements of the Invention. In some embodiments, the invention provides:

1. A pharmaceutical composition comprising an amorphous solid dispersion of triptolide and one or more pharmaceutically acceptable excipients, wherein the composition has a single glass transition temperature.
2. The pharmaceutical composition of Statement 1, wherein the composition remains amorphous per x-ray diffraction analysis following storage in an open container at about 40° C., relative humidity of about 75%, at five weeks.
3. The pharmaceutical composition of Statement 1 or 2, wherein the one or more pharmaceutically acceptable excipients comprises one or more polymers, a processing agent and/or a surfactant.
4. The pharmaceutical composition of Statement 3, wherein the one or more pharmaceutical polymers comprises an agent selected from the group consisting of sodium carboxymethyl-cellulose, poly(vinyl acetate)-co-polyvinylpyrrolidone) copolymer, ethylcellulose, hydroxypropylcellulose, cellulose acetate butyrate, poly(vinylpyrrolidone), poly(ethylene glycol), poly(ethylene oxide), poly(vinyl alcohol), hydroxypropyl methylcellulose, ethylcellulose, hydroxyethylcellulose, dimethylaminoethyl methacrylate-methacrylic acid ester copolymer, ethylacrylate-methylmethacrylate copolymer, cellulose acetate phthalate, cellulose acetate trimelletate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropylmethylcellulose acetate succinate and polyvinyl caprolactam-polyvinyl acetate-polyethylene glycol graft copolymer.
5. The pharmaceutical composition of Statement 3, wherein the surfactant comprises an agent selected from the group consisting of sodium dodecyl sulfate, dioctyl sodium sulphosuccinate, polyoxyethylene (20) sorbitan monooleate, glycerol polyethylene glycol oxystearate-fatty acid glycerol polyglycol esters-polyethylene glycols-glycerol ethoxylate, glycerol-polyethylene glycol ricinoleate-fatty acid esters of polyethyleneglycol-polyethylene glycols-ethoxylated glycerol, vitamin E TPGS, and sorbitan laurate, and the pharmaceutical polymer comprises an agent selected from a group consisting of poly(vinylpyrrolidone), hydroxypropylcellulose, poly(vinyl alcohol), hydroxypropyl methylcellulose, hydroxyethylcellulose, and sodium carboxymethyl-cellulose and polyvinyl caprolactam-polyvinyl acetate-polyethylene glycol graft copolymer.
6. The pharmaceutical composition of Statement 3, wherein the one or more pharmaceutical polymers is/are a water-soluble polymer(s).
7. The pharmaceutical composition of Statement 6, wherein the one or more pharmaceutical water soluble polymer(s) is/are selected from the group consisting of hydroxypropylmethylcellulose acetate succinate, cellulose, poly(vinyl acetate)-co-poly(vinylpyrrolidone) copolymer, poly(vinylpyrrolidone), cellulose acetate phthalate, poly(vinyl acetate) phthalate, hydroxypropylmethylcellulose phthalate, poly(methacrylate ethylacrylate) (1:1) copolymer, poly(methacrylate methylmethacrylate) (1:1) copolymer, poly(methacrylate methylmethacrylate) (1:2) copolymer, hydroxypropyl methylcellulose, poly(vinyl alcohol), and polyvinyl caprolactam-polyvinyl acetate-polyethylene glycol graft copolymer.
8. The pharmaceutical composition of Statement 6, wherein the triptolide to water soluble pharmaceutical polymer ratio is about 2:3, 1:1, or 3:2, or alternatively about 1:5 to about 1:10, or about 1:7.
9. The pharmaceutical composition of any one of Statements 1-8, wherein the composition exhibits a drug loading of about 1%-60% triptolide, about 40%-60% triptolide, about 30% triptolide, 35% triptolide, 40% triptolide, 45% triptolide, 50% triptolide, 55% triptolide, or 60% triptolide.
10. The pharmaceutical composition of any one of Statements 1-9, wherein the composition has less than about 1.0% degradation products of triptolide.
11. The pharmaceutical composition of any one of Statements 1-10, wherein the purity of triptolide used in the composition is about 95%, about 99%, about 99.5%, or about 95% to about 100%.
12. The pharmaceutical composition of any one of Statements 1-11, wherein the pharmaceutical composition does not contain a processing agent, and/or does not contain a plasticizer.
13. The pharmaceutical composition of any one of Statements 1-12, wherein the pharmaceutical composition comprises about 0.5 mg, about 1 mg triptolide, about 2 mg triptolide, about 5 mg triptolide, about 9 mg triptolide, about 12.5 mg triptolide, about 25 mg triptolide, about 36 mg triptolide, or about 50 mg triptolide.
14. The pharmaceutical composition of any one of Statements 1-13, wherein the one or more pharmaceutically acceptable excipients comprises a pharmaceutical polymer of high melt viscosity or a thermally labile pharmaceutical polymer.
15. The pharmaceutical composition of any one of Statements 1-14, wherein the purity of the composition is about 95%, about 99%, about 99.5%, or about 95% to about 100%.
16. The pharmaceutical composition of any one of Statements 1-15, wherein the peak solubility of the triptolide in the composition is greater than 4 g/mL in an aqueous buffer with a pH range of 4 to 8.
17. The pharmaceutical composition of any one of Statements 1-16, wherein peak solubility of a triptolide and the reference standard triptolide after an 8 hour dissolution test in an aqueous buffer with a pH range of 4 to 8 have a ratio of greater than 4:1.

18. The pharmaceutical composition of any one of Statements 1-17, wherein in the AUC of the triptolide in the composition and AUC of a reference standard triptolide have a ratio that is greater than 4:3.
19. The pharmaceutical composition of any one of Statements 1-18, wherein the composition is formulated as an oral dosage form.
20. The pharmaceutical composition of Statement 19, wherein the oral dosage form is a tablet, a capsule, or a sachet.
21. The pharmaceutical composition of Statement 20, wherein the tablet is a round flat tablet, a round concave tablet, an elongated tablet, or a minitab.
22. The pharmaceutical composition of Statement 20, wherein the oral dosage form is an extended-release form, an immediate release form, a disintegrating tablet or an eroding tablet.
23. The pharmaceutical composition of any one of Statements 1-22, wherein the one or more pharmaceutically acceptable excipients comprises a lubricant.
24. The pharmaceutical composition of Statement 23, wherein the lubricant is magnesium stearate.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Triptolide Kinetisol Solid Dispersion

The KinetiSol amorphous solid dispersion (KSD) triptolide tablet improves solubility, bioavailability (BA), and stability compared to a solid tablet of triptolide or a triptolide pro-drug that is not a KSD. The KSD triptolide tablet contains 0.25 mg or 0.5 mg of triptolide.

Immediate release tablets containing 0.25 mg and 0.5 mg triptolide were prepared by the method described by U.S. Pat. No. 8,486,423 (Brough) and U.S. Pat. No. 10,265,301 (Miller) (wherein deferasirox is replaced with triptolide), and in particular, US Publication No. 2020/0009060 (Miller), as a KinetiSol solid dispersion (KSD) with hydroxypropyl-methylcellulose acetate succinate (HPMCAS) high melting point (HMP), milled and screened <60 mesh, and tableted into 50 mg and 150 mg tablets.

KSD Tablet Composition (TRP TAB).

| Component | % w/w |
|---|---|
| Triptolide | 1.0 |
| HPMCAS-HMP | 38.8 |
| Microcrystalline Cellulose | 37.0 |
| Mannitol | 15.0 |
| Croscarmellose Sodium | 7.0 |
| Colloidal Silica | 0.5 |
| Magnesium Stearate | 0.7 |

The resulting off-white tablet is amorphous by XRPD and has total impurities of less than about 2% (specifically, less than or equal to 0.05%) as determined by HPLC.

The sodium croscarmellose (internally cross-linked sodium carboxymethylcellulose) acts a disintegrant of the triptolide, and inclusion of magnesium stearate in the tablet (as a lubricant) decreases the dissolution rate of triptolide but increases its bioavailability. The magnesium stearate can optionally be combined with, or replaced by, sodium stearyl fumarate, as the lubricant of the formulation.

The KSD triptolide tablet (TRP_TAB) was used for the PK analysis to develop the data illustrated in FIGS. 1-6.

Example 2

Triptolide PK Analysis

Methods.

Triptolide concentration data were provided for 4 beagle dogs who received single doses of triptolide 0.5 mg tablet (see Example 1) on Day 1 and minnelide 0.5 mg capsule on Day 4. Each dog was numbered as 100× on Day 1 and 200× on Day 4; however, only the 100× numbers are shown in these results to clearly indicate the same dog received both treatments.

Dogs were fasted overnight before each dose and food was provided after the 4-hour (h) sample was collected. There was one 4.0-h sample which was not collected under fasted conditions: dog 1002, for whom the 4.0-h sample after Minnelide capsule administration had to be collected a second time due to inadequate volume. Since food was provided to the dog after the initial sample collection, the dog was no longer fasting when the second sample was collected. Both samples were processed and sent to the laboratory, and the results provided did not indicate which sample was analyzed.

The noncompartmental pharmacokinetic analysis was performed as described in the protocol, including setting concentrations below the limit of quantitation (BLQ) to zero and calculating AUC values using the linear trapezoidal linear interpolation method. The lower limit of quantitation was 1.00 ng/mL.

After the primary analysis was reviewed by the sponsor, a secondary analysis excluding Dog 1004 was performed. Drug absorption from the tablet formulation appeared to be delayed for Dog 1004 since $C_{max}$ was lower and $t_{max}$ occurred later (3.0 h) than in the other dogs. Results from both analyses are included in summary data.

Data.

The PK Analysis Results of the four dog study are shown in FIGS. 1-3. Data excluding Dog 1004 are shown in FIGS. 4-6.

Figure 1A:
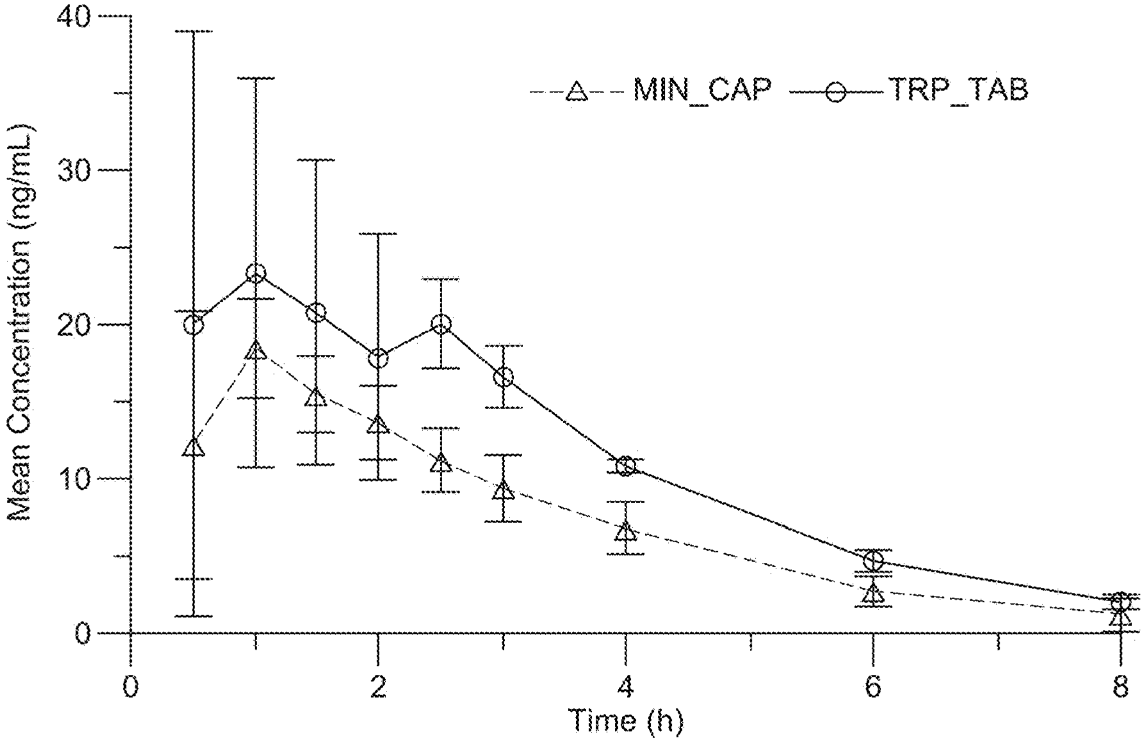
FIG. 1A-B. PK Analysis Results: Mean Triptolide Concentration vs Time Profiles. MIN_CAP=minnelide capsule (N=4); TRP_TAB=triptolide tablet (N=4). A: Linear Scale; B: Semilogarithmic Scale.
Figure 1B:
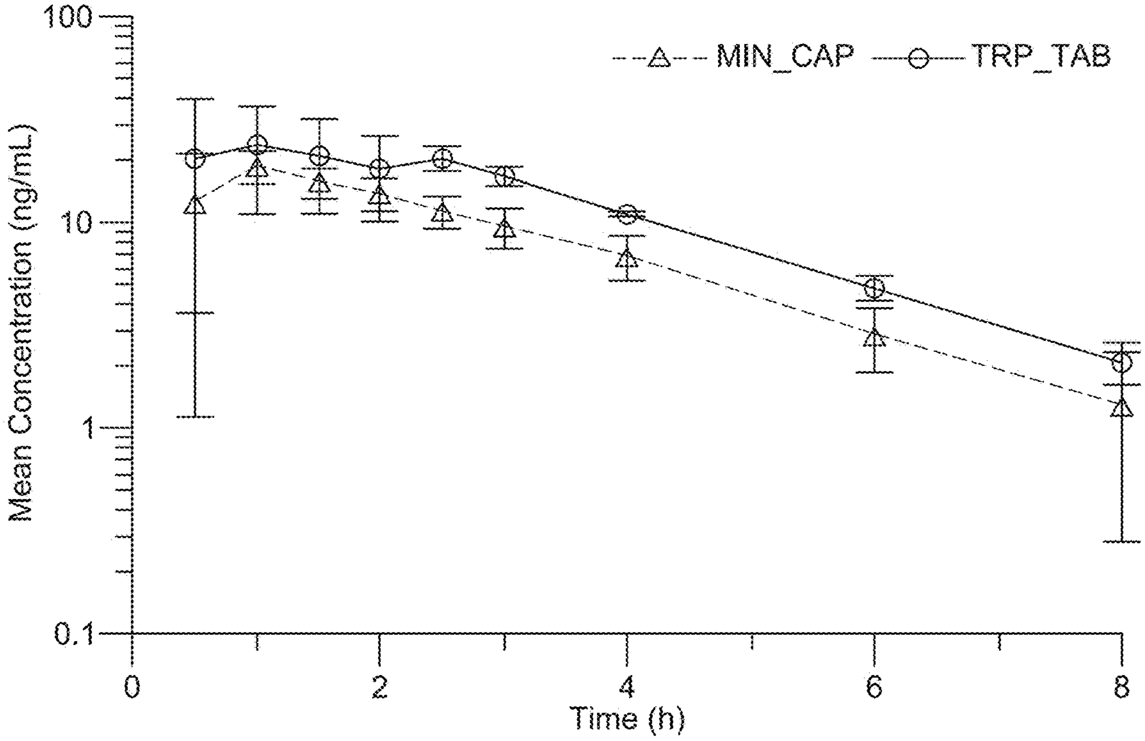

Mean Triptolide Concentration vs Time Profiles are shown in FIG. 1A-B. Tables 1 and 2 show the relevant data used for the creation of FIGS. 1-3.

TABLE 1

Triptolide Concentration Summary.

| Treatment | Dose (mg) | Dog | 0.50 | 1.00 | 1.50 | 2.00 | 2.50 | 3.00 | 4.00 | 6.00 | 8.00 |
|---|---|---|---|---|---|---|---|---|---|---|---|
| | | | Hour (h) | | | | | | | | |
| | | | Concentration (ng/ml) | | | | | | | | |
| MIN_CAP | 0.50 | 1001 | 12.32 | 23.02 | 18.91 | 17.14 | 14.07 | 12.16 | 9.3 | 4.24 | 2.44 |
| | | 1002 | 0 | 16 | 14.59 | 12.61 | 11.25 | 9.73 | 6.24 | 2.77 | 1.38 |
| | | 1003 | 17.1 | 18.82 | 15.57 | 13.36 | 10.36 | 8.86 | 6.28 | 2.28 | 1.32 |
| | | 1004 | 19.58 | 16.4 | 12.97 | 11.65 | 9.16 | 7.05 | 5.58 | 2.03 | 0 |
| | | N | 4 | 4 | 4 | 4 | 4 | 4 | 4 | 4 | 4 |
| | | Mean | 12.251 | 18.559 | 15.510 | 13.689 | 11.211 | 9.446 | 6.851 | 2.830 | 1.285 |
| | | SD | 8.706 | 3.224 | 2.509 | 2.404 | 2.092 | 2.124 | 1.667 | 0.992 | 1.000 |
| | | CV % | 71.1 | 17.4 | 16.2 | 17.6 | 18.7 | 22.5 | 24.3 | 35.1 | 77.8 |
| | | Min | 0.00 | 16.00 | 12.97 | 11.65 | 9.16 | 7.05 | 5.58 | 2.03 | 0.00 |
| | | Median | 14.710 | 17.608 | 15.079 | 12.984 | 10.805 | 9.290 | 6.263 | 2.524 | 1.349 |
| | | Max | 19.58 | 23.02 | 18.91 | 17.14 | 14.07 | 12.16 | 9.30 | 4.24 | 2.44 |
| TRP_TAB | 0.50 | 1001 | 37.14 | 30.47 | 24.26 | 20.54 | 17.59 | 15.17 | 10.84 | 4.88 | 2.20 |
| | | 1002 | 3.62 | 27.69 | 28.01 | 23.59 | 19.90 | 15.68 | 10.36 | 4.68 | 1.90 |
| | | 1003 | 35.84 | 30.71 | 24.86 | 21.31 | 24.17 | 16.07 | 10.87 | 5.56 | 2.68 |
| | | 1004 | 3.69 | 4.68 | 6.15 | 6.30 | 18.72 | 19.57 | 11.43 | 3.96 | 1.54 |
| | | N | 4 | 4 | 4 | 4 | 4 | 4 | 4 | 4 | 4 |
| | | Mean | 20.071 | 23.386 | 20.820 | 17.934 | 20.094 | 16.622 | 10.873 | 4.771 | 2.078 |
| | | SD | 18.963 | 12.549 | 9.919 | 7.862 | 2.874 | 1.999 | 0.439 | 0.657 | 0.483 |
| | | CV % | 94.5 | 53.7 | 47.6 | 43.8 | 14.3 | 12.0 | 4.0 | 13.8 | 23.3 |
| | | Min | 3.62 | 4.68 | 6.15 | 6.30 | 17.59 | 15.17 | 10.36 | 3.96 | 1.54 |
| | | Median | 19.763 | 29.081 | 24.560 | 20.922 | 19.308 | 15.872 | 10.855 | 4.779 | 2.047 |
| | | Max | 37.14 | 30.71 | 28.01 | 23.59 | 24.17 | 19.57 | 11.43 | 5.56 | 2.68 |

Concentrations for the 2 samples with concentrations below the limit of quantitation were set 0.00. Dogs are identified by the 100× number to clearly indicate the same dog received both treatments.

TABLE 2

Triptolide Pharmacokinetic Parameters.

| Treatment | Dose (mg) | Dog | Cmax (ng/ml) | tmax (h) | Cmax/Dose (ng/ml/mg) | AUCtlast (h * ng/mL) | AUCtlast/Dose (h * ng/ml/mg) | tlast (h) |
|---|---|---|---|---|---|---|---|---|
| MIN_CAP | 1 0.5 | 1001 | 23.02 | 1.0 | 46.04 | 76.74 | 153.48 | 8.0 |
| | | 1002 | 16.00 | 1.0 | 32.00 | 50.80 | 101.60 | 8.0 |
| | | 1003 | 18.82 | 1.0 | 37.63 | 59.54 | 119.09 | 8.0 |
| | | 1004 | 19.58 | 0.5 | 39.17 | 50.56 | 101.12 | 6.0 |
| | | N | 4 | 4 | 4 | 4 | 4 | 4 |
| | | Mean | 19.355 | 0.88 | 38.711 | 59.410 | 118.820 | 7.50 |
| | | SD | 2.888 | 0.25 | 5.777 | 12.285 | 24.569 | 1.00 |
| | | CV % | 14.9 | 28.6 | 14.9 | 20.7 | 20.7 | 13.3 |
| | | Min | 16.00 | 0.5 | 32.00 | 50.56 | 101.12 | 6.0 |
| | | Median | 19.200 | 1.00 | 38.400 | 55.172 | 110.344 | 8.00 |
| | | Max | 23.02 | 1.0 | 46.04 | 76.74 | 153.48 | 8.0 |
| TRP_TAB | 0.5 | 1001 | 37.14 | 0.5 | 74.27 | 104.59 | 209.17 | 8.0 |
| | | 1002 | 28.01 | 1.5 | 56.03 | 89.96 | 179.92 | 8.0 |
| | | 1003 | 35.84 | 0.5 | 71.68 | 110.60 | 221.20 | 8.0 |
| | | 1004 | 19.57 | 3.0 | 39.14 | 61.05 | 122.10 | 8.0 |
| | | N | 4 | 4 | 4 | 4 | 4 | 4 |
| | | Mean | 30.139 | 1.38 | 60.278 | 91.548 | 183.096 | 8.00 |
| | | SD | 8.117 | 1.18 | 16.235 | 22.102 | 44.205 | 0.00 |
| | | CV % | 26.9 | 85.9 | 26.9 | 24.1 | 24.1 | 0.0 |
| | | Min | 19.57 | 0.5 | 39.14 | 61.05 | 122.10 | 8.0 |
| | | Median | 31.926 | 1.00 | 63.851 | 97.272 | 194.543 | 8.00 |
| | | Max | 37.14 | 3.0 | 74.27 | 110.60 | 221.20 | 8.0 |

Since concentrations below the limit of quantitation were set to zero, the values for t and tlast were the same; therefore, $AUC_{0-t}$ and $AUC_{0-t}$/Dose were not reported. Dogs are identified by the 100× number to clearly indicated the same dog received both treatments.

Triptolide Concentration vs Time Profiles for Individual Dogs (Linear Scale) are shown in FIG. 2A-B. Triptolide Concentration vs Time Profiles for Individual Dogs (Semi-logarithmic Scale) are shown in FIG. 3A-B. The data of FIGS. 2 and 3 show that the triptolide tablets provide superior bioavailability compared to the prodrug minnelide capsules.

Data without Dog 1004. The PK Analysis Results of study omitting Dog 1004 are shown in FIGS. 4-6.

Mean Triptolide Concentration vs Time Profiles are shown in FIG. 4A-B. Tables 3 and 4 show the relevant data used for the creation of FIGS. 4-6.

TABLE 3

| Triptolide Concentration Summary (N = 3). | | | | | | | | | | | |
|---|---|---|---|---|---|---|---|---|---|---|---|
| | | | Hour (h) | | | | | | | | |
| | Dose | | 0.50 | 1.00 | 1.50 | 2.00 | 2.50 | 3.00 | 4.00 | 6.00 | 8.00 |
| Treatment | (mg) | Dog | Concentration (ng/ml) | | | | | | | | |
| MIN_CAP | 0.50 | 1001 | 12.32 | 23.02 | 18.91 | 17.14 | 14.07 | 112.16 | 9.30 | 4.24 | 2.44 |
| | | 1002 | 0.00 | 16.00 | 14.59 | 12.61 | 11.25 | 9.73 | 6.24 | 2.77 | 1.38 |
| | | 1003 | 17.10 | 18.82 | 15.57 | 13.36 | 10.36 | 8.86 | 6.28 | 2.28 | 1.32 |
| | | N | 3 | 3 | 3 | 3 | 3 | 3 | 3 | 3 | 3 |
| | | Mean | 9.807 | 19.279 | 16.357 | 14.369 | 11.895 | 10.246 | 7.277 | 3.097 | 1.713 |
| | | SD | 8.823 | 3.533 | 2.268 | 2.427 | 1.940 | 1.712 | 1.756 | 1.023 | 0.632 |
| | | CV % | 90.0 | 18.3 | 13.9 | 16.9 | 16.3 | 16.7 | 24.1 | 33.0 | 36.9 |
| | | Min | 0.00 | 16.00 | 14.59 | 12.61 | 10.36 | 8.86 | 6.24 | 2.28 | 1.32 |
| | | Median | 12.320 | 18.816 | 15.570 | 13.357 | 11.254 | 9.725 | 6.283 | 2.770 | 1.377 |
| | | Max | 17.10 | 23.02 | 18.91 | 17.14 | 14.07 | 12.16 | 9.30 | 4.24 | 2.44 |
| TRP_TAB | 0.50 | 1001 | 37.14 | 30.47 | 24.26 | 20.54 | 17.59 | 15.17 | 10.84 | 4.88 | 2.20 |
| | | 1002 | 3.62 | 27.69 | 28.01 | 23.59 | 19.90 | 15.68 | 10.36 | 4.68 | 1.90 |
| | | 1003 | 35.84 | 30.71 | 24.86 | 21.31 | 24.17 | 16.07 | 10.87 | 5.56 | 2.68 |
| | | N | 3 | 3 | 3 | 3 | 3 | 3 | 3 | 3 | 3 |
| | | Mean | 25.533 | 29.623 | 25.711 | 21.811 | 20.552 | 15.639 | 10.688 | 5.040 | 2.258 |
| | | SD | 18.985 | 1.678 | 2.016 | 1.587 | 3.336 | 0.448 | 0.289 | 0.462 | 0.394 |
| | | CV % | 74.4 | 5.7 | 7.8 | 7.3 | 16.2 | 2.9 | 2.7 | 9.2 | 17.4 |
| | | Min | 3.62 | 27.69 | 24.26 | 20.54 | 17.59 | 15.17 | 10.36 | 4.68 | 1.90 |
| | | Median | 35.839 | 30.472 | 24.856 | 21.306 | 19.899 | 15.676 | 10.838 | 4.877 | 2.196 |
| | | Max | 37.14 | 30.71 | 28.01 | 23.59 | 24.17 | 16.07 | 10.87 | 5.56 | 2.68 |

The concentration for the 1 sample with concentration below the limit of quantitation was set 0.00. Dogs are identified by the 100× number to clearly indicate the same dog received both treatments.

Results.

At each time point, the mean triptolide concentration was higher for the triptolide tablet than for the minnelide capsule, both with and without Dog 1004.

TABLE 4

| Triptolide Pharmacokinetic Parameters (N = 3). | | | | | | | | |
|---|---|---|---|---|---|---|---|---|
| Treatment | Dose (mg) | Dog | Cmax (ng/mL) | tmax (h) | Cmax/Dose (ng/ml/mg) | AUCtlast (h * ng/ml) | AUCtlast/Dose (h * ng/ml/mg) | tlast (h) |
| MIN_CAP | 0.5 | 1001 | 23.02 | 1.0 | 46.04 | 76.74 | 153.48 | 8.0 |
| | | 1002 | 16.00 | 1.0 | 32.00 | 50.80 | 101.60 | 8.0 |
| | | 1003 | 18.82 | 1.0 | 37.63 | 59.54 | 119.09 | 8.0 |
| | | N | 3 | 3 | 3 | 3 | 3 | 3 |
| | | Mean | 19.279 | 1.000 | 38.558 | 62.361 | 124.722 | 8.000 |
| | | SD | 3.533 | 0.000 | 7.065 | 13.196 | 26.392 | 0.000 |
| | | CV % | 18.3 | 0.0 | 18.3 | 21.2 | 21.2 | 0.0 |
| | | Min | 16.00 | 1.00 | 32.00 | 50.80 | 101.60 | 8.0 |
| | | Median | 18.816 | 1.00 | 37.632 | 59.543 | 119.085 | 8.000 |
| | | Max | 23.02 | 1.00 | 46.04 | 76.74 | 153.48 | 8.00 |
| TRP_TAB | 0.5 | 1001 | 37.14 | 0.5 | 74.27 | 104.59 | 209.17 | 8.0 |
| | | 1002 | 28.01 | 1.5 | 56.03 | 89.96 | 179.92 | 8.0 |
| | | 1003 | 35.84 | 0.5 | 71.68 | 110.60 | 221.20 | 8.0 |
| | | N | 3 | 3 | 3 | 3 | 3 | 3 |
| | | Mean | 33.662 | 0.833 | 67.324 | 101.714 | 203.428 | 8.000 |
| | | SD | 4.935 | 0.577 | 9.871 | 10.615 | 21.231 | 0.000 |
| | | CV % | 14.7 | 69.3 | 14.7 | 10.4 | 10.4 | 0.0 |
| | | Min | 28.01 | 0.50 | 56.03 | 89.96 | 179.92 | 8.00 |
| | | Median | 35.839 | 0.50 | 71.677 | 104.585 | 209.170 | 8.000 |
| | | Max | 37.14 | 1.50 | 74.27 | 110.60 | 221.20 | 8.00 |

Since concentrations below the limit of quantitation were set to zero, the values for t and tlast were the same; therefore, $AUC_{0-t}$ and $AUC_{0-t}$/Dose were not reported. Dogs are identified by the 100× number to clearly indicate the same dog received both treatments.

Triptolide Concentration vs Time Profiles for Individual Dogs (Linear Scale) are shown in FIG. 5A-B. Triptolide Concentration vs Time Profiles for Individual Dogs (Semi-logarithmic Scale) are shown in FIG. 6A-B. The data of FIGS. 5 and 6 show that the triptolide tablets provide superior bioavailability compared to the prodrug minnelide capsules.

When all dogs were included, mean triptolide $C_{max}$ and $AUC_{tlast}$ were 56% and 54% higher, respectively, for the triptolide tablet than for the minnelide capsule. Variability in $C_{max}$ was greater for the tablet than the capsule (CV %: 26.9% vs 14.9%), while variability in $AUC_{tlast}$ was similar for both formulations (24.1% vs 20.7%).

When Dog 1004 was excluded, mean triptolide $C_{max}$ and $AUC_{tlast}$ were 75% and 63% higher, respectively, for the triptolide tablet than for the minnelide capsule. Variability was similar for both formulations for $C_{max}$ (CV %: 14.7% vs 18.3%), and greater for the capsule than the tablet for $AUC_{tlast}$ (21.2% vs 10.4%).

Median $t_{max}$ was 1.0 hour for both formulations when all dogs were included in the analysis. When Dog 1004 was excluded, median $t_{max}$ was 1.00 h for the minnelide capsule and 0.5 h for the triptolide tablet.

The results from this pilot study indicate that the triptolide tablet is more bioavailable than the minnelide capsule.

All publications, patents, and patent documents cited herein are incorporated by reference as though individually incorporated by reference. No limitations inconsistent with this disclosure are to be understood therefrom. The invention has been described with reference to various specific and preferred embodiments and techniques. However, many variations and modifications may be made while remaining within the spirit and scope of the invention.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

What is claimed is:

1. A pharmaceutical composition consisting of:

a) about 38.8% w/w hydroxypropyl methyl cellulose acetate succinate (HPMCAS);

b) about 37% w/w microcrystalline cellulose;

c) about 15% w/w mannitol;

d) about 7% w/w crosslinked carboxymethyl cellulose sodium (croscarmellose sodium);

e) about 0.7% w/w of magnesium stearate;

f) about 0.5% colloidal silica; and g) about 0.1 mg to about 1 mg of triptolide;

wherein the composition is amorphous solid dispersion; and wherein the composition has a single glass transition temperature and the composition remains amorphous per x-ray diffraction analysis following storage in an open container at about 40° C. with a relative humidity of about 75% at five weeks.

2. The pharmaceutical composition of claim 1, wherein the composition consists of about 1% w/w triptolide.

3. The pharmaceutical composition of claim 1, wherein the pharmaceutical composition comprises about 0.1 mg of triptolide, about 0.15 mg of triptolide, about 0.2 mg of triptolide, about 0.25 mg of triptolide, about 0.4 mg of triptolide, about 0.5 mg of triptolide, or about 0.6 mg of triptolide.

4. The pharmaceutical composition of claim 1, wherein the pharmaceutical composition consists of particles of mesh size less than about 60.

5. The pharmaceutical composition of claim 1, wherein the pharmaceutical composition further consists of sodium stearyl fumarate.

6. The pharmaceutical composition of claim 1, wherein the pharmaceutical composition is formulated as an oral dosage form.

7. The pharmaceutical composition of claim 6, wherein the oral dosage form is a tablet.

8. The pharmaceutical composition of claim 6, wherein the oral dosage form is an immediate release form.

9. A method of treating cancer comprising administering to a cancer subject in need thereof an effective anticancer amount of the pharmaceutical composition of claim 1, thereby treating the cancer.

10. The method of claim 9, wherein the cancer comprises gastric cancer, pancreatic cancer, breast cancer, bladder cancer, kidney cancer, lung cancer, ovarian cancer, glioblastoma, or melanoma.

* * * * *